US005863744A

United States Patent [19]
Avraham et al.

[11] Patent Number: 5,863,744
[45] Date of Patent: Jan. 26, 1999

[54] NEURAL CELL PROTEIN MARKER RR/B AND DNA ENCODING SAME

[75] Inventors: Shalom Avraham; Hava Avraham; Jerome E. Groopman, all of Brookline, Mass.

[73] Assignee: New England Deaconess Hospital Corporation, Boston, Mass.

[21] Appl. No.: 317,305

[22] Filed: Oct. 3, 1994

[51] Int. Cl.$^6$ .................................................. G01N 33/53
[52] U.S. Cl. .................. 435/7.21; 530/387.9; 530/388.1; 530/388.85
[58] Field of Search ............................. 530/387.9, 388.1, 530/388.85, 389.1; 435/4, 7.1, 7.21, 7.23

[56] References Cited

PUBLICATIONS

Adams, M., et al., "3,400 New Expressed Sequence Tags Identify Diversity of Transcripts in Human Brain," *Nature Genetics*, vol. 4, 256–267 (1993).

International Search Report for PCT/US95/12508 issued Jan. 11, 1996.

Sambrook, J., et al., "Molecular Cloning, A Laboratory Manual," Cold Spring Harbor Laboratory Press, 16.1–16.81 (1989).

Arnheiter, H., et al., "Physicochemical and Antigenic Properties of Synthetic Fragments of Human Leukocyte Interferon," *Nature*, vol. 294, 278–280 (1981).

Bantle, J. and Hahn, W., "Complexity and Characterization of Polyadenylated RNA in the Mouse Brain," *Cell*, vol. 8, 139–150 (1976).

Guillemin, R., "Peptides in the Brain: The New Endocrinology of the Neuron," *Science*, vol. 202, 390–402 (1978).

Hastie, N. and Bishop J., "The Expression of Three Abundance Classes of Messenger RNA in Mouse Tissue," *Cell*, vol. 9, 761–774 (1976).

Purves, D. and Lichtman, J., *Principles of Neural Development*, Sinauer Associates Inc., MA, 263–267 (1985).

Purves et al., Principles of Neural Development, published 1985 by Sinauer Assoc. Inc., MA. pp. 263–267.

*Primary Examiner*—Marianne P. Allen
*Assistant Examiner*—Patricia A. Duffy
*Attorney, Agent, or Firm*—Lahive & Cockfield

[57] ABSTRACT

The invention contemplates the novel neural cell protein marker RR/B, cDNA encoding RR/B, nucleic acid probes for detection of mRNA encoding RR/B, synthetic polypeptides whose sequences correspond to a portion of RR/B and have a molecular weight equal to less than that of RR/B, and methods for detection of RR/B.

5 Claims, 19 Drawing Sheets

ATGTCAGTCAGTGTGCATGAGAACCGCAAGTCCAGGGCCAGCAGCGGCTCCATTAACATCTATCT
GTTTCACAAGTCCTCCTACGCTGACAGCGTCCTCACTCACCTGAATCTTTTACGCCAGCAGCGTC
TCTTCACTGACGTCCTTCTCCATGCCGGAAATAGGACCTTCCCTTGCCACCGGGCAGTGCTGGCT
GCATGCAGTCGCTACTTTGAGGCCATGTTCAGTGGTGGCCTGAAAGAGAGCCAGGACAGTGAGGT
CAACTTTGACAATTCCATCCACCCAGAAGTCTTGGAGCTGCTGCTTGACTATGCGTACTCCTCCC
GGGTCATCATCAATGAAGAAATGCAGAATCGCTCCTGGAAGCTGGTGACATGCTGGAGTTTCAA
GACATCCGGGATGCATGTGCAGAGTTCCTGGAAAAGAACCTGCATCCCACCAACTGCCTGGGCAT
GCTGCTGCTGTCTGATGCACACCAGTGCACCAAGCTGTACGAACTATCTTGGAGAATGTGTCTCA
GCAACTTCCAAACCATCAGGAAGAATGAAGATTTCCTCCAGCTGCCCCAGGACATGGTAGTGCAA
CTCTTGTCCAGTGAAGAGCTGGAGACAGAGGATGAAAGGCTTGTGTACGAGTCTGCAATTAACTG
GATCAGCTATGACCTGAAGAAGCGCTATTGCTACCTCCCAGAACTGTTGCAGACAGTAAGGCTGG
CACTTCTGCCAGCCATCTATCTCATGGAGAATGTGGCCATGGAGGAACTCATCACCAAGCAGAGA
AAGAGTAAGGAAATTGTGGAAGAGGCCATCAGGTGCAAACTGAAAATCCTGCAGAATGACGGTGT
GGTAACCAGCCTCTGTGCCCGACCTCGGAAAACTGGCCATGCCCTCTTCCTTCTGGGAGGACAGA
CTTTCATGTGTGACAAGTTGTATCTGGTAGACCAGAAGGCCAAAGAAATCATTCCCAAGGCTGAC
ATTCCCAGCCCAAGAAAAGAGTTTAGTGCATGTGCGATTGGCTGCAAAGTGTACATTACTGGGGG
GCGGGGGTCTGAAAATGGGGTCTCGAAAGATGTCTGGGTTTATGATACCCTGCACGAGGAGTGGT
CCAAGGCTGCCCCCATGCTGGTGGCCAGGTTTGGCCATGGCTCTGCTGAACTGAAGCACTGCCTG
TATGTGGTTGGGGGGCACACGGCCGCAACTGGCTGCCTCCCGGCCTCCCCCTCAGTCTCTCTAAA
GCAGGTAGAACATTATGACCCCACAATCAACAAATGGACCATGGTGGCCCCACTCCGAGAAGGCG
TTAGCAACGCCGCAGTAGTGAGTGCCAAACTTAAGTTATTTGCTTTCGGAGGTACCAGTGTCAGT
CATGACAAGCTCCCCAAAGTTCAGTGTTACGATCAGTGTGAAAACAGGTGGACTGTACCGGCCAC
CTGTCCCCAGCCCTGGCGTTACACAGCAGCAGCTGTGCTGGGGAACCAGATTTTTATTATGGGGG
GTGATACAGAATTCTCTGCCTGCTCTGCTTATAAATTCAACAGTGAGACTTACCAGTGGACCAAA

FIG. 1A

GTGGGAGATGTGACAGCAAAGCGCATGAGCTGCCATGCTGTGGCCTCTGGAAACAAACTCTACGT
GGTTGGAGGATACTTTGGCATTCAGCGATGCAAGACTTTGGACTGCTACGATCCAACATTAGACG
TGTGGAACAGCATCACCACTGTCCCGTACTCGCTGATTCCTACTGCATTTGTCAGCACCTGGAAA
CATCTGCCTTCTTAA

*FIG. 1A-1*

MSVSVHENRKSRASSGSINIYLFHKSSYADSVLTHLNLLRQQRLFTDVLLHAGNRTFPCH
RAVLAACSRYFEAMFSGGLKESQDSEVNFDNSIHPEVLELLLDYAYSSRVIINEENAESL
LEAGDMLEFQDIRDACAEFLEKNLHPTNCLGMLLLSDAHQCTKLYELSWRMCLSNFQTIR
KNEDFLQLPQDMVVQLLSSEELETEDERLVYESAMNWISYDLKKRYCYLPELLQTVRLAL
LPAIYLMENVAMEELITKQRKSKEIVEEAIRCKLKILQNDGVVTSLCARPRKTGHALFLL
GGQTFMCDKLYLVDQKAKEIIPKADIPSPRKEFSACAIGCKVYITGGRGSENGVSKDVWV
YDTLHEEWSKAAPMLVARFGHGSAELKHCLYVVGGHTAATGCLPASPSVSLKQVEQYDPT
TNKWTMVAPLREGVSNAAVVSAKLKLFAFGGTSVSHDKLPKVQCYDQCENRWSVPATCPQ
PWRYTAAAVLGNQIFIMGGDTEFSACSAYKFNSETYQWTKVGDVTAKRMSCHAVASGNKL
YVVGGYFGIQRCKTLDCYDPTLDVWNSITTVPYSLIPTAFVSTWKHLPS

*FIG. 1B*

```
ATGTCAGTCAGTGTGCATGAGAACCGCAAGTCCAGGGCCAGCAGTGGCTCCATCAACATCTACCT
GTTTCATAAGTCCTCCTACGCGGACAGCGTTCTCACTCACCTGAACCTTCTGCGTCAGCAGCGGC
TCTTCACAGATGTCCTTCTCCATGCGGGAAACAGGACCTTCCCTTGCCACCGGGCAGTGCTGGCT
GCGTGCAGCCGCTACTTCGAAGCCATGTTCAGTGGTGGCCTGAAAGAGAGCCAGGACAGTGAGGT
GAACTTCGACAATTCCATCCACCCAGAAGTCTTAGAGCTGCTTCTAGACTACGCATACTCCTCCC
GGGTCATTATCAATGAAGAAATGCTGAGTCGCTCCTGGAGGCTGGTGACATGCTGGAGTTCCAG
GACATCAGAGATGCGTGTGCAGAATTTCTAGAGAAGAACCTGCATCCCACCAACTGCCTGGGTAT
GCTGCTGTTGTCTGATGCCCACCAGTGCACCAAGCTGTACGAACTCTCCTGGAGAATGTGTCTCA
GCAACTTCCAAACCATTCGGAAGAACGAAGATTTCCTCCAGTTGCCCCAGGACATGGTTGTGCAG
CTGCTGTCCAGTGAAGAACTGGAGACGGAAGACGAAAGGCTGGTGTATGAGTCTGCGATGAACTG
GATCAGCTATGACCTGAAGAAGCGCTACTGTTACCTCCCGGAACTGTTGCAGACAGTGAGGCTGG
CCCTCCTTCCTGCCATCTATCTCATGGAGAACGTGGCGATGGAAGAACTCATCACCAAGCAGAGA
AAGAGTAAGGAGATCGTGGAAGAGGCCATCAGGTGCAAACTAAAAATCTTACAGAATGACGGCGT
GGTCACCAGTCTCTGTGCTCGTCCTCGGAAAACTGGCCATGCCCTGTTCCTCCTGGGAGGGCAGA
CTTTCATGTGTGACAAACTGTACTTGGTAGACCAGAAGGCTAAGAAATCATTCCCAAGGCTGAC
ATTCCCAGCCCGAGGAAAGAGTTCAGCGCATGTGCAATTGGCTGCAAAGTATATATTACTGGGGG
GCGGGGATCAGAGAACGGAGTCTCAAAAGATGTCTGGGTTTACGATACCCTGCATGAGGAGTGGT
CCAAGGCTGCCCCCATGCTGGTGGCCAGGTTTGGCCATGGATCTGCTGAACTGAAGCACTGCCTC
TATGTAGTCGGTGGGCACACAGCTGCAACTGGCTGCCTCCCAGCCTCCCCCTCGGTCTCCCTAAA
GCAAGTAGAACAGTATGACCCCACAACCAACAAATGGACCATGGTAGCCCCACTCCGCGAAGGTG
TCAGCAATGCTGCTGTAGTGAGTGCCAAACTTAAGCTGTTTGCTTTCGGGGGTACCAGTGTGAGC
CACGACAAGCTGCCCAAGGTTCAGTGTTACGATCAATGCGAGAACAGATGGTCAGTGCCGGCCAC
CTGTCCCCAGCCCTGGCGTTACACAGCCGCAGCTGTGCTGGGAAACCAGATTTTTATCATGGGTG
GAGATACAGAGTTCTCTGCCTGCTCCGCTTACAAATTCAATAGTGAGACTTACCAGTGGACCAAG
```

*FIG. 2*

GTGGGAGATGTGACAGCCAAGCGCATGAGCTGCCACGCCGTGGCGTCCGGGAACAAGCTTTACGT
AGTTGGAGGGTACTTCGGCATTCAGCGCTGCAAGACTTTGGACTGTTACGACCCAACTTTAGATG
TGTGGAACAGCATAACCACTGTTCCCTACTCTCTGATCCCTACTGCATTCGTCAGCACCTGGAAA
CACCTGCCTTCCTAA

*FIG. 2-1*

MSVSVHENRKSRASSGSINIYLFHKSSYADSVLTHLNLLRQQRLFTDVLLHAGNRTFPCH
RAVLAACSRYFEAMFSGGLKESQDSEVNFDNSIHPEVLELLLDYAYSSRVIINEENAESL
LEAGDMLEFQDIRDACAEFLEKNLHPTNCLGMLLLSDAHQCTKLYELSWRMCLSNFQTIR
KNEDFLQLPQDMVVQLLSSEELETEDERLVYESAINWISYDLKKRYCYLPELLQTVRLAL
LPAIYLMENVAMEELITKQRKSKEIVEEAIRCKLKILQNDGVVTSLCARPRKTGHALFLL
GGQTFMCDKLYLVDQKAKEIIPKADIPSPRKEFSACAIGCKVYITGGRGSENGVSKDVWV
YDTLHEEWSKAAPMLVARFGHGSAELKHCLYVVGGHTAATGCLPASPSVSLKQVEHYDPT
INKWTMVAPLREGVSNAAVVSAKLKLFAFGGTSVSHDKLPKVQCYDQCENRWTVPATCPQ
PWRYTAAAVLGNQIFIMGGDTEFSACSAYKFNSETYQWTKVGDVTAKRMSCHAVASGNKL
YVVGGYFGIQRCKTLDCYDPTLDVWNSITTVPYSLIPTAFVSTWKHLPS

*FIG. 3*

```
                     1                                                                 39
Human       ATGTCAGTC  AGTGTGCATG  AGAACCGCAA  GTCCAGGGCC
Mouse       ATGTCAGTC  AGTGTGCATG  AGAACCGCAA  GTCCAGGGCC
Consensus   ATGTCAGTC  AGTGTGCATG  AGAACCGCAA  GTCCAGGGCC 40                                                                                     89
AGCAGCGGCT  CCATTAACAT  CTATCTGTTT  CACAAGTCCT  CCTACGCTGA
AGCAGTGGCT  CCATCAACAT  CTACCTGTTT  CATAAGTCCT  CCTACGCGGA
AGCAG-GGCT  CCAT-AACAT  CTA-CTGTTT  CA-AAGTCCT  CCTACGC-GA 90                                                                                    139
CAGCGTCCTC  ACTCACCTGA  ATCTTTTACG  CCAGCAGCGT  CTCTTCACTG
CAGCGTTCTC  ACTCACCTGA  ACCTTCTGCG  TCAGCAGCGG  CTCTTCACAG
CAGCGT-CTC  ACTCACCTGA  A-CTT-T-CG  -CAGCAGCG-  CTCTTCAC-G 140                                                                                   189
ACGTCCTTCT  CCATGCCGGA  AATAGGACCT  TCCCTTGCCA  CCGGGCAGTG
ATGTCCTTCT  CCATGCGGGA  AACAGGACCT  TCCCTTGCCA  CCGGGCAGTG
A-GTCCTTCT  CCATGC-GGA  AA-AGGACCT  TCCCTTGCCA  CCGGGCAGTG 190                                                                                   239
CTGGCTGCAT  GCAGTCGCTA  CTTTGAGGCC  ATGTTCAGTG  GTGGCCTGAA
CTGGCTGCGT  GCAGCCGCTA  CTTCGAAGCC  ATGTTCAGTG  GTGGCCTGAA
CTGGCTGC-T  GCAG-CGCTA  CTT-GA-GCC  ATGTTCAGTG  GTGGCCTGAA 240                                                                                   289
AGAGAGCCAG  GACAGTGAGG  TCAACTTTGA  CAATTCCATC  CACCCAGAAG
AGAGAGCCAG  GACAGTGAGG  TGAACTTCGA  CAATTCCATC  CACCCAGAAG
AGAGAGCCAG  GACAGTGAGG  T-AACTT-GA  CAATTCCATC  CACCCAGAAG 290                                                                                   339
TCTTGGAGCT  GCTGCTTGAC  TATGCGTACT  CCTCCCGGGT  CATCATCAAT
TCTTAGAGCT  GCTTCTAGAC  TACGCATACT  CCTCCCGGGT  CATTATCAAT
TCTT-GAGCT  GCT-CT-GAC  TA-GC-TACT  CCTCCCGGGT  CAT-ATCAAT 340                                                                                   389
GAAGAAAATG  CAGAATCGCT  CCTGGAAGCT  GGTGACATGC  TGGAGTTTCA
GAAGAAAATG  CTGAGTCGCT  CCTGGAGGCT  GGTGACATGC  TGGAGTTCCA
GAAGAAAATG  C-GA-TCGCT  CCTGGA-GCT  GGTGACATGC  TGGAGTT-CA 390                                                                                   439
AGACATCCGG  GATGCATGTG  CAGAGTTCCT  GGAAAAGAAC  CTGCATCCCA
GGACATCAGA  GATGCGTGTG  CAGAATTTCT  AGAGAAGAAC  CTGCATCCCA
-GACATC-G-  GATGC-TGTG  CAGA-TT-CT  -GA-AAGAAC  CTGCATCCCA 440                                                                                   489
CCAACTGCCT  GGGCATGCTG  CTGCTGTCTG  ATGCACACCA  GTGCACCAAG
CCAACTGCCT  GGGTATGCTG  CTGTTGTCTG  ATGCCCACCA  GTGCACCAAG
CCAACTGCCT  GGG-ATGCTG  CTG-TGTCTG  ATGC-CACCA  GTGCACCAAG
```

*FIG. 4*

```
490                                                                 539
CTGTACGAAC TATCTTGGAG AATGTGTCTC AGCAACTTCC AAACCATCAG
CTGTACGAAC TCTCCTGGAG AATGTGTCTC AGCAACTTCC AAACCATTCG
CTGTACGAAC T-TC-TGGAG AATGTGTCTC AGCAACTTCC AAACCAT--G 540                                                                 589
GAAGAATGAA GATTTCCTCC AGCTGCCCCA GGACATGGTA GTGCAACTCT
GAAGAACGAA GATTTCCTCC AGTTGCCCCA GGACATGGTT GTGCAGCTGC
GAAGAA-GAA GATTTCCTCC AG-TGCCCCA GGACATGGT- GTGCA-CT--

590                                                                 639
TGTCCAGTGA AGAGCTGGAG ACAGAGGATG AAAGGCTTGT GTACGAGTCT
TGTCCAGTGA AGAACTGGAG ACGGAAGACG AAAGGCTGGT GTATGAGTCT
TGTCCAGTGA AGA-CTGGAG AC-GA-GA-G AAAGGCT-GT GTA-GAGTCT 640                                                                 689
GCAATTAACT GGATCAGCTA TGACCTGAAG AAGCGCTATT GCTACCTCCC
GCGATGAACT GGATCAGCTA TGACCTGAAG AAGCGCTACT GTTACCTCCC
GC-AT-AACT GGATCAGCTA TGACCTGAAG AAGCGCTA-T G-TACCTCCC 690                                                                 739
AGAACTGTTG CAGACAGTAA GGCTGGCACT TCTGCCAGCC ATCTATCTCA
GGAACTGTTG CAGACAGTGA GGCTGGCCCT CCTTCCTGCC ATCTATCTCA
-GAACTGTTG CAGACAGT-A GGCTGGC-CT -CT-CC-GCC ATCTATCTCA 740                                                                 789
TGGAGAATGT GGCCATGGAG GAACTCATCA CCAAGCAGAG AAAGAGTAAG
TGGAGAACGT GGCGATGGAA GAACTCATCA CCAAGCAGAG AAAGAGTAAG
TGGAGAA-GT GGC-ATGGA- GAACTCATCA CCAAGCAGAG AAAGAGTAAG 790                                                                 839
GAAATTGTGG AAGAGGCCAT CAGGTGCAAA CTGAAAATCC TGCAGAATGA
GAGATCGTGG AAGAGGCCAT CAGGTGCAAA CTAAAAATCT TACAGAATGA
GA-AT-GTGG AAGAGGCCAT CAGGTGCAAA CT-AAAATC- T-CAGAATGA 840                                                                 889
CGGTGTGGTA ACCAGCCTCT GTGCCCGACC TCGGAAAACT GGCCATGCCC
CGGCGTGGTC ACCAGTCTCT GTGCTCGTCC TCGGAAAACT GGCCATGCCC
CGG-GTGGT- ACCAG-CTCT GTGC-CG-CC TCGGAAAACT GGCCATGCCC 890                                                                 939
TCTTCCTTCT GGGAGGACAG ACTTTCATGT GTGACAAGTT GTATCTGGTA
TGTTCCTCCT GGGAGGGCAG ACTTTCATGT GTGACAAACT GTACTTGGTA
T-TTCCT-CT GGGAGG-CAG ACTTTCATGT GTGACAA--T GTA--TGGTA 940                                                                 989
GACCAGAAGG CCAAAGAAAT CATTCCCAAG GCTGACATTC CCAGCCCAAG
GACCAGAAGG CTAAAGAAAT CATTCCCAAG GCTGACATTC CCAGCCCGAG
GACCAGAAGG C-AAAGAAAT CATTCCCAAG GCTGACATTC CCAGCCC-AG
```

*FIG. 4-1*

```
990                                                                1039
AAAAGAGTTT AGTGCATGTG CGATTGGCTG CAAAGTGTAC ATTACTGGGG
GAAAGAGTTC AGCGCATGTG CAATTGGCTG CAAAGTATAT ATTACTGGGG
-AAAGAGTT- AG-GCATGTG C-ATTGGCTG CAAAGT-TA- ATTACTGGGG 1040                                                               1089
GGCGGGGGTC TGAAAATGGG GTCTCGAAAG ATGTCTGGGT TTATGATACC
GGCGGGGATC AGAGAACGGA GTCTCAAAAG ATGTCTGGGT TTACGATACC
GGCGGGG-TC -GA-AA-GG- GTCTC-AAAG ATGTCTGGGT TTA-GATACC 1090                                                               1139
CTGCACGAGG AGTGGTCCAA GGCTGCCCCC ATGCTGGTGG CCAGGTTTGG
CTGCATGAGG AGTGGTCCAA GGCTGCCCCC ATGCTGGTGG CCAGGTTTGG
CTGCA-GAGG AGTGGTCCAA GGCTGCCCCC ATGCTGGTGG CCAGGTTTGG 1140                                                               1189
CCATGGCTCT GCTGAACTGA AGCACTGCCT GTATGTGGTT GGGGGGCACA
CCATGGATCT GCTGAACTGA AGCACTGCCT CTATGTAGTC GGTGGGCACA
CCATGG-TCT GCTGAACTGA AGCACTGCCT -TATGT-GT- GG-GGGCACA 1190                                                               1239
CGGCCGCAAC TGGCTGCCTC CCGGCCTCCC CCTCAGTCTC TCTAAAGCAG
CAGCTGCAAC TGGCTGCCTC CCAGCCTCCC CCTCGGTCTC CCTAAAGCAA
C-GC-GCAAC TGGCTGCCTC CC-GCCTCCC CCTC-GTCTC -CTAAAGCA- 1240                                                               1289
GTAGAACATT ATGACCCCAC AATCAACAAA TGGACCATGG TGGCCCCACT
GTAGAACAGT ATGACCCCAC AACCAACAAA TGGACCATGG TAGCCCCACT
GTAGAACA-T ATGACCCCAC AA-CAACAAA TGGACCATGG T-GCCCCACT 1290                                                               1339
CCGAGAAGGC GTTAGCAACG CCGCAGTAGT GAGTGCCAAA CTTAAGTTAT
CCGCGAAGGT GTCAGCAATG CTGCTGTAGT GAGTGCCAAA CTTAAGCTGT
CCG-GAAGG- GT-AGCAA-G C-GC-GTAGT GAGTGCCAAA CTTAAG-T-T 1340                                                               1389
TTGCTTTCGG AGGTACCAGT GTCAGTCATG ACAAGCTCCC CAAAGTTCAG
TTGCTTTCGG GGGTACCAGT GTGAGCCACG ACAAGCTGCC CAAGGTTCAG
TTGCTTTCGG -GGTACCAGT GT-AG-CA-G ACAAGCT-CC CAA-GTTCAG 1390                                                               1439
TGTTACGATC AGTGTGAAAA CAGGTGGACT GTACCGGCCA CCTGTCCCCA
TGTTACGATC AATGCGAGAA CAGATGGTCA GTGCCGGCCA CCTGTCCCCA
TGTTACGATC A-TG-GA-AA CAG-TGG-C- GT-CCGGCCA CCTGTCCCCA 1440                                                               1489
GCCCTGGCGT TACACAGCAG CAGCTGTGCT GGGGAACCAG ATTTTTATTA
GCCCTGGCGT TACACAGCCG CAGCTGTGCT GGGAAACCAG ATTTTTATCA
GCCCTGGCGT TACACAGC-G CAGCTGTGCT GGG-AACCAG ATTTTTAT-A
```

*FIG. 4-2*

```
1490                                                        1539
TGGGGGGTGA TACAGAATTC TCTGCCTGCT CTGCTTATAA ATTCAACAGT
TGGGTGGAGA TACAGAGTTC TCTGCCTGCT CCGCTTACAA ATTCAATAGT
TGGG-GG-GA TACAGA-TTC TCTGCCTGCT C-GCTTA-AA ATTCAA-AGT 1540                                                        1589
GAGACTTACC AGTGGACCAA AGTGGGAGAT GTGACAGCAA AGCGCATGAG
GAGACTTACC AGTGGACCAA GGTGGGAGAT GTGACAGCCA AGCGCATGAG
GAGACTTACC AGTGGACCAA -GTGGGAGAT GTGACAGC-A AGCGCATGAG 1590                                                        1639
CTGCCATGCT GTGGCCTCTG GAAACAAACT CTACGTGGTT GGAGGATACT
CTGCCACGCC GTGGCGTCCG GGAACAAGCT TTACGTAGTT GGAGGGTACT
CTGCCA-GC- GTGGC-TC-G G-AACAA-CT -TACGT-GTT GGAGG-TACT 1640                                                        1689
TTGGCATTCA GCGATGCAAG ACTTTGGACT GCTACGATCC AACATTAGAC
TCGGCATTCA GCGCTGCAAG ACTTTGGACT GTTACGACCC AACTTTAGAT
T-GGCATTCA GCG-TGCAAG ACTTTGGACT G-TACGA-CC AAC-TTAGA- 1690                                                        1739
GTGTGGAACA GCATCACCAC TGTCCCGTAC TCGCTGATTC CTACTGCATT
GTGTGGAACA GCATAACCAC TGTTCCCTAC TCTCTGATCC CTACTGCATT
GTGTGGAACA GCAT-ACCAC TGT-CC-TAC TC-CTGAT-C CTACTGCATT 1740                          1770
TGTCAGCACC TGGAAACATC TGCCTTCTTA A
CGTCAGCACC TGGAAACACC TGCCTTCCT. A
-GTCAGCACC TGGAAACA-C TGCCTTC-T- A
```

*FIG. 4-3*

```
1                                                                    60
MSVSVHENRK  SRASSGSINI  YLFHKSSYAD  SVLTHLNLLR  QQRLFTDVLL  HAGNRTFPCH

MSVSVHENRK  SRASSGSINI  YLFHKSSYAD  SVLTHLNLLR  QQRLFTDVLL  HAGNRTFPCH 61                                                                   120
RAVLAACSRY  FEAMFSGGLK  ESQDSEVNFD  NSIHPEVLEL  LLDYAYSSRV  IINEENAESL

RAVLAACSRY  FEAMFSGGLK  ESQDSEVNFD  NSIHPEVLEL  LLDYAYSSRV  IINEENAESL 121                                                                  180
LEAGDMLEFQ  DIRDACAEFL  EKNLHPTNCL  GMLLLSDAHQ  CTKLYELSWR  MCLSNFQTIR

LEAGDMLEFQ  DIRDACAEFL  EKNLHPTNCL  GMLLLSDAHQ  CTKLYELSWR  MCLSNFQTIR 181                                                                  240
KNEDFLQLPQ  DMVVQLLSSE  ELETEDERLV  YESAINWISY  DLKKRYCYLP  ELLQTVRLAL

KNEDFLQLPQ  DMVVQLLSSE  ELETEDERLV  YESAMNWISY  DLKKRYCYLP  ELLQTVRLAL 241                                                                  300
LPAIYLMENV  AMEELITKQR  KSKEIVEEAI  RCKLKILQND  GVVTSLCARP  RKTGHALFLL

LPAIYLMENV  AMEELITKQR  KSKEIVEEAI  RCKLKILQND  GVVTSLCARP  RKTGHALFLL 301                                                                  360
GGQTFMCDKL  YLVDQKAKEI  IPKADIPSPR  KEFSACAIGC  KVYITGGRGS  ENGVSKDVWV

GGQTFMCDKL  YLVDQKAKEI  IPKADIPSPR  KEFSACAIGC  KVYITGGRGS  ENGVSKDVWV 361                                                                  420
YDTLHEEWSK  AAPMLVARFG  HGSAELKHCL  YVVGGHTAAT  GCLPASPSVS  LKQVEHYDPT

YDTLHEEWSK  AAPMLVARFG  HGSAELKHCL  YVVGGHTAAT  GCLPASPSVS  LKQVEQYDPT 421                                                                  480
INKWTMVAPL  REGVSNAAVV  SAKLKLFAFG  GTSVSHDKLP  KVQCYDQCEN  RWTVPATCPQ

TNKWTMVAPL  REGVSNAAVV  SAKLKLFAFG  GTSVSHDKLP  KVQCYDQCEN  RWSVPATCPQ
```

*FIG. 5*

```
481                                                                      540
PWRYTAAAVL GNQIFIMGGD TEFSACSAYK FNSETYQWTK VGDVTAKRMS CHAVASGNKL

PWRYTAAAVL GNQIFIMGGD TEFSACSAYK FNSETYQWTK VGDVTAKRMS CHAVASGNKL 541                                               590
YVVGGYFGIQ RCKTLDCYDP TLDVWNSITT VPYSLIPTAF VSTWKHLPS

YVVGGYFGIQ RCKTLDCYDP TLDVWNSITT VPYSLIPTAF VSTWKHLPS
```

*FIG. 5-1*

NEURAL CELL PROTEIN MARKER RR/B AND DNA ENCODING SAME

FIELD OF THE INVENTION

The invention relates to protein markers of neural tissue.

BACKGROUND OF THE INVENTION

A key to understanding the function of any tissue is the biochemical characterization of the proteins that are specific to that tissue. Mammalian neural tissue is composed of two predominant cell types, neurons and glia, which are organized into a great variety of structures. Whether neural tissue is viewed as one or several tissues, its organization involves many cells that are believed generally to perform the same physiological actions but at different places and in response to different signals. Accordingly, one can expect to find a large number of neural tissue-specific proteins in both undifferentiated and differentiated neural tissue, including those involved in both specialized and general processes.

Exemplary of specifiable neural tissue-specific proteins are: neuropeptide precursors, enzymes responsible for neurotransmitter synthesis and/or processing, and proteins that participate in the release, degradation or reuptake of neurotransmitters, signal receptor systems and ion channels. Proteins included in the basic cellular structures encompass those peculiar to neurons (axons, dendrites and synapses) and those involved in establishing specific cell-cell interactions. Also, there will be proteins involved in mental processes such as memory which are not at all yet understood at the cellular, let alone molecular level. Clearly, nervous system tissue is a difficult tissue to study at the molecular level due to its great complexity.

Mature mammalian neurons are incapable of cell division and cannot, with the exception of olfactory neurons, be generated from stem cells in the adult nervous system. Thus, continuous dividing clonal cell lines with neuronal characteristics have proven to be very useful to neurobiologists studying almost every aspect of the nervous system. Such cell lines allow the generation of large numbers of homogeneous cells and the manipulation of these cells through gene transfer to yield novel derivatives expressing foreign gene products. These advantages have led to development and characterization of a variety of neuronal cell lines, some of which have been useful for cellular, biochemical, and molecular studies. The utility of these different cell lines and their ability to approximate aspects of the neuronal phenotype vary widely. Rapidly dividing neuronal cell lines usually do not possess the phenotypic properties of terminally differentiated non-dividing neurons, instead they often resemble in vivo neuroblasts or embryonic neurons. For example, many rapidly dividing cell lines elaborate immature neurites with an immature cytoskeleton. Naturally occurring neoplastic derivatives of many neuronal cell types of the central (CNS) and peripheral (PNS) nervous systems usually fall within this category (e.g., neuroblastomas, pheochromocytomas and medulloblastomas).

It is presumed that all of the proteins of the nervous system are synthesized by translation from specific messenger RNA (mRNA) molecules, and thus each neural tissue-specific protein must have a corresponding mRNA. Thus, one approach to the study of the nervous system is through the transcription pattern of mRNA molecules, or by asking the question of what messenger RNA species neural tissue produces relative to its complete genomic potential. Estimates for the complexity of mammalian neural tissue-specific mRNAs are very high; tens to hundreds of thousands of discrete mRNA molecules are implicated in nervous system function (Bantle et al., Cell, 8, 39–150, 1976, and Hastie et al., Cell 9, 761–774, 1976), consistent with the variety of neural tissue-specific proteins listed above.

It is an object of the invention to provide a unique protein marker of neural tissue, and a nucleic acid encoding the protein.

Yet another object of the invention is to provide a novel protein marker of certain neuronal tumor cell lines.

Yet another object of the invention is to provide a novel protein marker of both neuroblastoma and glioblastoma cells.

Yet another object of the invention is to provide a novel protein marker of cells of both the central and peripheral nervous system.

Yet another object of the invention is to provide antibodies specific for a novel protein marker present on neural tissue.

Another object of the invention is to provide probes for detection of a novel protein marker, or its corresponding mRNA, that is more abundant in normal neural tissue than in neoplastic tissue.

SUMMARY OF THE INVENTION

The invention is based on the discovery of a novel protein, RR/B, that is detectable in neuronal cell lines derived from both central and peripheral nervous tissue, a nucleic acid sequence encoding RR/B, antibodies specific for RR/B, and methods for detection of RR/B or its coding nucleic acid.

Thus, in one aspect, the invention features an isolated DNA comprising the nucleotide sequence presented in SEQ ID NO: 1.

The invention also features an isolated DNA selected from the group consisting of: (a) an isolated DNA comprising a DNA sequence that encodes the amino acid sequence presented in SEQ ID NO: 2; and (b) an isolated DNA capable of hybridizing to the complement of a DNA according to (a) above under moderately stringent hybridization conditions and which encodes the amino acid sequence of SEQ ID NO: 2.

As used herein, the term "hybridization" refers to conventional DNA/DNA hybridization conditions. For example, for a probe of about 10–50 nucleotides, moderately stringent hybridization conditions are preferred and include 10× SSC, 5× Denhardts, 0.1% SDS, at 35–50 degrees for 15 hours; for a probe of about 50–300 nucleotides, "stringent" hybridization conditions are preferred and refer to hybridization in 6× SSC, 5× Denhardts, 0.1% SDS at 65 degrees for 15 hours.

The invention also encompasses recombinant expression vectors comprising a nucleic acid or isolated DNA encoding RR/B and a process for preparing RR/B, comprising culturing a suitable host cell comprising the vector under conditions suitable for promoting expression of RR/B, and recovering said RR/B.

The invention also features a nucleic acid probe comprising 10 consecutive nucleotides presented in SEQ ID NO: 1.

Preferably, the probe may comprise 15, 20, 50, 100, 200, and 300, etc., consecutive nucleotides presented in SEQ ID NO: 1.

In another aspect, the invention features a purified protein comprising an amino acid sequence encoded by DNA comprising the nucleotide sequence presented in SEQ ID NO: 1.

This aspect of the invention also encompasses a purified protein comprising the amino acid sequence encoded by DNA comprising a nucleotide sequence hybridizable under moderately stringent conditions to the nucleotide sequence presented in SEQ ID NO: 1.

The invention also features a synthetic polypeptide corresponding in amino acid residue sequence to at least a portion of the sequence of naturally occurring RR/B, and having a molecular weight equal to less than 60 kd. A synthetic polypeptide of the invention is useful for inducing the production of antibodies specific for the synthetic polypeptide and that bind to naturally occurring RR/B.

Preferred embodiments of this aspect of the invention include a group of synthetic polypeptides whose members correspond to a fragment of the RR/B protein comprising the sequence: S-S-E-E-L-E-T-E-D-E-R-L-V amino acid residues 198 to 210 and K-Q-R-K-S-K-E-I-V-E-E-A-I amino acid residues 258 to 270 of SEQ ID NO: 2.

The invention also features a monoclonal antibody specific for an epitope of RR/B, said RR/B comprising the amino acid sequence presented in SEQ ID NO: 2.

Preferably, the antibody is specific for an epitope specified by the amino acid residues 198 to 210 (S-S-E-E-L-E-T-E-D-E-R-L-V) (P1) or amino acid residues 258 to 270 (K-Q-R-K-S-K-E-I-V-E-E-A-I) (P2) of SEQ ID NO: 2.

The invention also features a method of assaying for the presence of RR/B in a sample of mammalian cells, comprising the steps of: (a) providing an antibody specific for said RR/B; and (b) assaying for the presence of said RR/B by admixing an aliquot from a sample of said mammalian cells with said antibody under conditions sufficient to allow for formation and detection of an immune complex of said RR/B and said antibody. Such method is useful for detecting neural tissue versus most other tissue types of the body, as well as for detecting normal neural tissue versus neoplastic neural tissue.

Preferably, this method includes providing a monoclonal antibody specific for an epitope that is antigenically the same, as determined by Western blot assay, ELISA or immunocytochemical staining, and substantially corresponds in amino acid sequence to the amino acid sequence of a portion of said RR/B and having a molecular weight equal to less than that of said RR/B.

More preferably, the epitope comprises an amino acid sequence selected from the group consisting of: amino acid residues 198 to 210 (S-S-E-E-L-E-T-E-D-E-R-L-V) and amino acid residues 258 to 270 (K-Q-R-K-S-K-E-F-V-E-E-A-I) of SEQ ID NO: 2.

The invention also features a method of assaying for the presence of RNA encoding RR/B in a sample of mammalian tissue as an indicator of the presence of neural tissue in said sample, comprising the steps of: (a) providing a nucleic acid probe hybridizable under moderately stringent conditions to RNA encoding the amino acid sequence of SEQ ID NO: 2; and (b) assaying for the presence of said RNA by admixing an aliquot from a sample of said mammalian tissue with said nucleic acid probe under conditions sufficient to allow detection of a hybrid formed between said nucleic acid probe and said RNA.

Preferably, the nucleic acid probe comprises a nucleotide sequence of 10, 15, 20, 50, 100, etc., consecutive nucleotides presented in SEQ ID NO: 1.

As used herein, "RR/B" refers to a 60 Kd protein having the amino acid sequence presented in SEQ ID NO: 2, that is present on both neuroblastoma and glioblastoma cells, and is not present on most other tissue types in the body (e.g., lung, liver, and heart tissues), and that is encoded by a messenger RNA that is present in at least 100-fold more abundance in non-neoplastic tissue or cells than in neoplastic tissue or cells. Therefore, the RR/B protein is useful as a marker that distinguishes neural tissue from most other tissue types, and that distinguishes non-neoplastic tissue from neoplastic tissue. Because RR/B is present on both neuroblastoma and glioblastoma cells, RR/B is a protein marker that may appear on neural cells prior to the developmental branch point that heralds the emergence of the two types of cells.

The invention thus also features a kit for detecting RR/B, the kit including at least one package containing an antibody or idiotype-containing polyamide portion of an antibody raised to a synthetic polypeptide of this invention or to a conjugate of that polypeptide bound to a carrier. An indicating group or label is utilized to indicate the formation of an immune reaction between the antibody and RR/B when the antibody is admixed with neural tissue or cells.

This aspect of the invention also features a kit for detection RNA encoding RR/B including at least one package containing a nucleic acid probe of at least 15 nucleotides that is hybridizable under moderate or stringent conditions to RNA encoding RR/B.

A diagnostic reagent that binds to neural tissue comprises yet another embodiment of the present invention. This reagent is an antibody that can be linked to an indicating group. The antibody or idiotype-containing portion of an antibody raised to a synthetic polypeptide or conjugate of that synthetic polypeptide bound to a carrier. An immune reaction is formed when the antibody is admixed with neural cell tissue that includes RR/B. The indicating group bound to the antibody or as an exogenously supplied reagent indicates the formation of an immune reaction between the antibody and neural tissue containing RR/B.

This aspect of the invention is the provision of a diagnostic system for assaying the presence of a naturally occurring amino acid residue sequence of a protein present in the neural cells, and of an antibody that immunologically reacts with neural cell tissues that include particular amino acid sequences.

Further features will become more fully apparent in the following description of the embodiments of this invention and from the appended claims.

BRIEF DESCRIPTION OF THE DRAWINGS

In the drawings:

FIGS. 1A and 1A-1 is the cDNA sequence of human RR/B cDNA (SEQ ID NO: 1).

FIG. 1B is the predicted amino acid sequence of human RR/B (SEQ ID NO: 2).

FIGS. 2 and 2-1 is the DNA sequence of murine brain RR/B cDNA (SEQ ID NO: 3).

FIG. 3 is the predicted amino acid sequence of murine RR/B (SEQ ID NO: 4).

FIGS. 4, 4-1, 4-2, and 4-3 is a comparison of the nucleotide sequences of human (SEQ ID NO: 1) and murine (SEQ ID NO: 3) RR/B.

FIGS. 5 and 5-1 is a comparison of the predicted amino acid sequences of human (SEQ ID NO: 2, top) and murine (SEQ ID NO: 4, bottom) RR/B.

DETAILED DESCRIPTION OF THE INVENTION

Figure 6A:
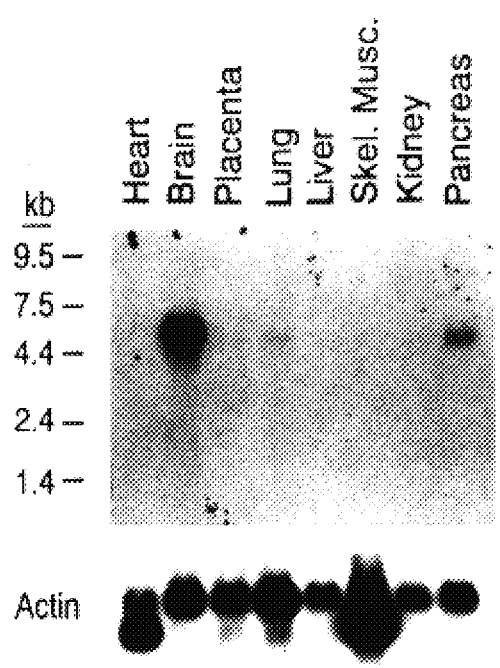
FIG. 6A is a Northern blot analysis of RR/B mRNA in human adult tissues.

The present invention contemplates the novel neural cell protein marker RR/B, cDNA encoding RR/B, nucleic acid probes for detection of mRNA encoding RR/B, and synthetic polypeptides whose sequences correspond to a portion of RR/B and have a molecular weight equal to less than that of the 60 kd RR/B.

RR/B is present abundantly in cells or cell lines of neural origin and megarkaryocytes relative to other cell types. This is in contradistinction to proteins such as somatostatin, thyrotropin-releasing factor (TRF), luteinizing hormone-releasing factor (LRF), the endorphins and enkephalins, or the several other small polypeptides such as bombesin, caerulein or physalamine that have been found to occur in the brain as well as in other tissues of the animal body. (Guillemin, Science 202, 390–402 (1978)).

The term "RR/B" is used herein to refer to the 60 kd direct polypeptide translation product of a messenger RNA having a complementary DNA sequence of SEQ ID NO: 1.

The phrase "RR/B derivative" is used herein to mean the polypeptide-containing material that results from cellular processing of RR/B. Thus, an RR/B derivative may therefore be a protein cleavage product of RR/B.

The phrase "immune reaction" is used herein to mean the binding of a ligand with its receptor and includes the binding between an antigen (ligand) with an antibody (receptor) as well as between an antigen and an idiotype-containing polyamide portion of an antibody (receptor). Similarly, "immune complex" refers to a complex consisting of the receptor (antibody) bound to its cognate antigen.

The phrase "corresponds substantially" as used herein in conjunction with amino acid sequences means that the amino acid sequence of a first polypeptide is sufficiently similar to the amino acid sequence contained in a second polypeptide so that antibodies to the first polypeptide (e.g. synthetic polypeptide) form an immune reaction with the second polypeptide (e.g. RR/B or RR/B derivative) when admixed in an aqueous medium. The preparation of such polypeptides and antibodies are discussed hereinafter.

The epitope-containing amino acid sequence portions of the above two polypeptides, e.g. synthetic polypeptide and RR/B protein, are most preferably identical, but conservative changes in amino acid residues and deletions or additions of amino acid residues within the epitope may be made and still permit the cross-reaction of an antibody to the first polypeptide with the second polypeptide, as is known. Conservative amino acid changes are well known, and include exchanges of residues such as between lysine and arginine, between aspartic acid and glutamic acid, between leucine and isoleucine, and between aspartic acid and glutamic acid, between leucine and isoleucine, and the like.

EXAMPLE I

The nucleotide sequences encoding human RR/B and mouse RR/B are presented in SEQ ID NOS: 1 and 3, respectively, corresponding to FIGS. 1A, 1A-1, 2, and 2-1, respectively.

Murine RR/B was cloned using 2.0 Kb of human RR/B cDNA as a probe to screen a mouse brain cDNA library under low stringency; about 15 clones were isolated. The nucleotide sequences of murine RR/B partial cDNA clones are shown in FIGS. 2 and 2-1, with 90% nucleotide sequence homology to human RR/B (FIGS. 4, 4-1, 4-2, and 4-3). Interestingly, the homology of the deduced amino acids between these two species is more than 99% (FIGS. 5 and 5-1). These results indicate that RR/B is a highly conserved gene in the human and mouse which might indicate an important role in cell—cell communication.

The homology of RR/B with the ring canal kelch gene is 28% between amino acid residues 562 to 1329. Lower homology of RR/B with other genes such as Vaccinia Virus A55R protein was found to be about 23% between amino acid 589 to 942. The homology of RR/B with the ring cell kelch gene at the nucleotide level is ~50% between nucleotide residues 577 to 2000.

Nucleic acid probes corresponding to portions of the sequence of human or mouse RR/B may be made according to conventional DNA synthesis techniques, and may be any length sufficient to allow formation of a stable hybrid, e.g., 10, 20, 50, 100, 300, etc., bases in length.

EXAMPLE II

The human and mouse RR/B amino acid sequences are presented in SEQ ID NOS: 2 and 4, respectively, and the sequences are compared in FIGS. 5 and 5-1.

Synthetic Polypeptides.

A synthetic polypeptide of the invention corresponds in amino acid sequence to at least a portion of the sequence of RR/B. Exemplary of such synthetic polypeptides are two synthetic polypeptides P1 and P2, discussed hereinbefore. That previous discussion illustrated that the sequences of the synthetic polypeptides corresponded substantially to portions of the sequences of the proteins translated by the cell from the cDNA sequence encoding RR/B shown in FIGS. 1A and 1A-1, and that the molecular weights of the synthetic polypeptides are substantially less than the molecular weight of RR/B itself.

EXAMPLE III

Interference with RR/B Synthesis using Antisense Oligonucleotides.

Figure 10:
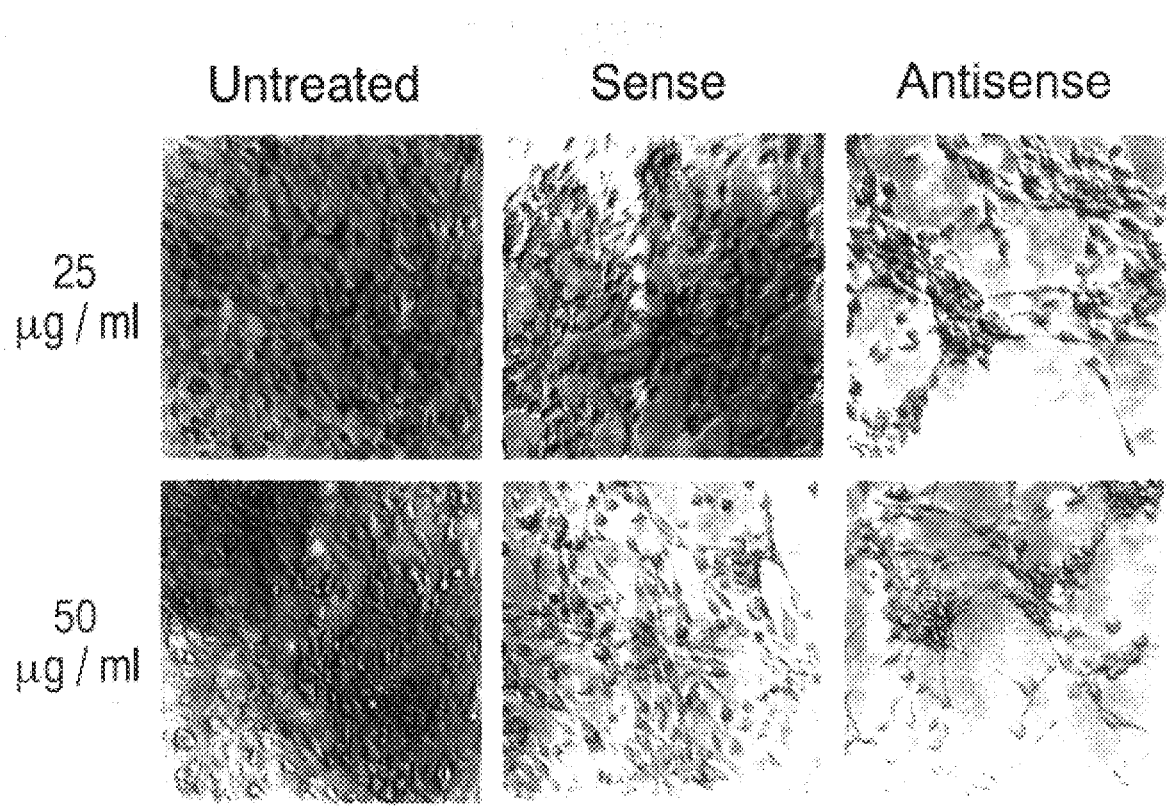
FIG. 10 is an autoradiogram of cultures having been treated with antisense RR/B oligonucleotides on cell—cell interactions and cell attachment. U373 cells were exposed to RR/B sense or antisense oligonucleotide 1B (corresponding to 211 nt–226 nt), at the indicated concentrations for 24 h and then assayed for [$^3$H]-thymidine incorporation, viability and morphological changes.

In an effort to determine the role of RR/B in brain, we examined the effects of blocking synthesis of RR/B proteins by RR/B antisense oligonucleotides on cell—cell interactions. Brain cell lines of glioblastomal U373 cells were treated with human RR/B sense or antisense phophorothiol oligonucleotides for 24 hr or 48 hr. Inhibition of glial cell—cell connections and also attachment of glial cells to plate matrix following RR/B antisense oligonucleotides treatment was observed (FIG. 10). U373 cells treated with antisense oligonucleotide 1B (corresponding to second amino acid to the eight amino acid), resulted in detachment and aggregation of cells compared to the attached and adherent monolayer of U373 cells untreated or treated with sense oligonucleotide 1B. These results indicate that RR/B may be involved in cell attachment to plate matrix and cell—cell interactions.

EXAMPLE IV

Figure 6B:
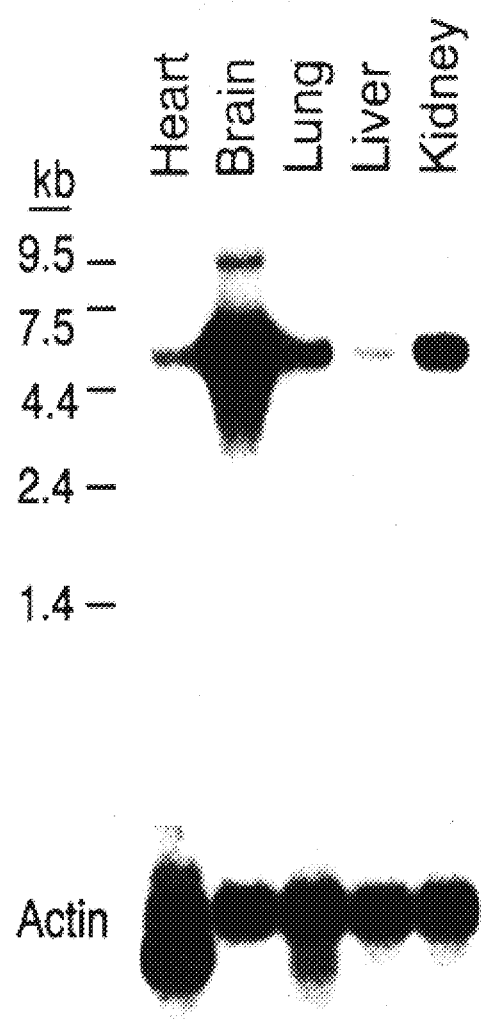
FIG. 6B is a Northern blot analysis of RR/B mRNA in human fetal tissues.
Figure 7:
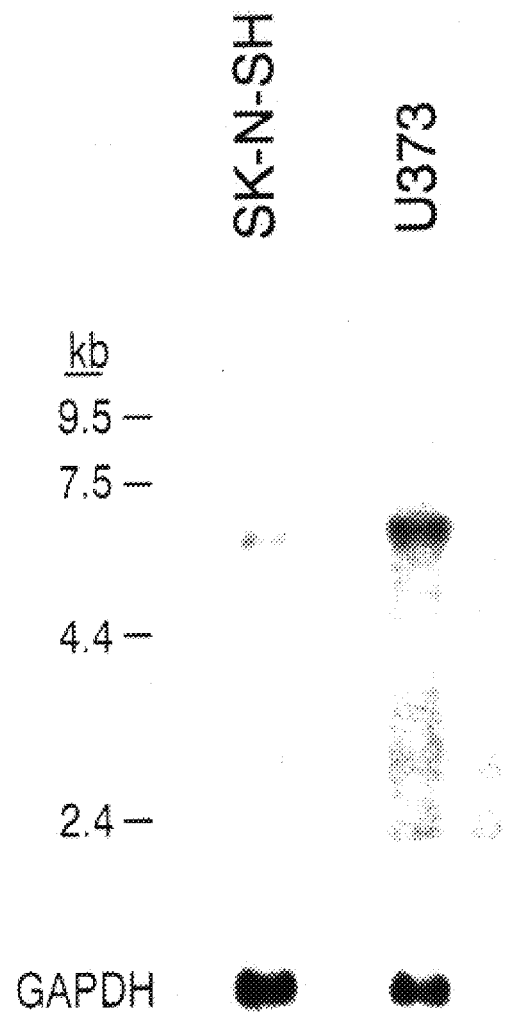
FIG. 7 is a Northern blot analysis of RR/B mRNA in glioblastoma and neuroblastoma cell lines.
Figure 8A:
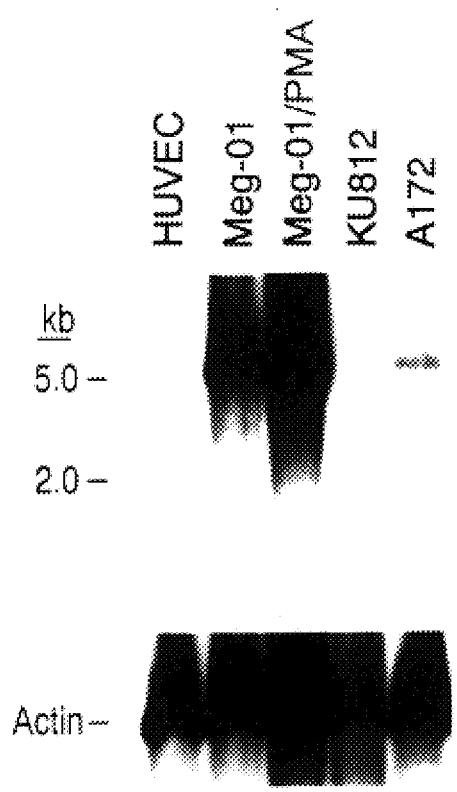
FIG. 8A is a Northern blot of RR/B mRNA in permanent megakaryocytic cell lines.
Figure 8B:
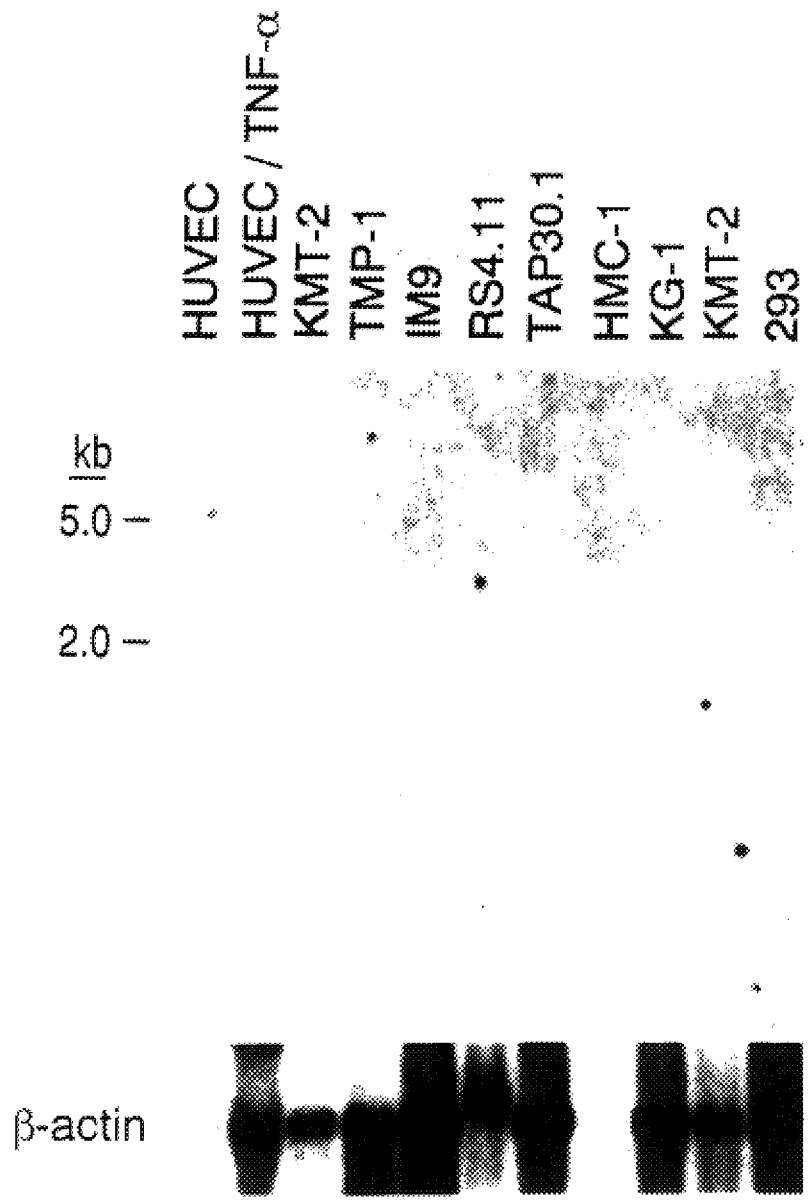
FIG. 8B is a Northern blot of RR/B mRNA in various permanent human cell lines.

A nucleic acid probe corresponding to residues 1351–1440 of the human RR/B nucleic acid sequence (SEQ ID NO: 1) was used to survey human cells lines and tissues for the presence of RR/B mRNA using Northern blot analysis. The results, presented in FIGS. 6A and 6B, revealed that RR/B mRNA is approximately 5.5 Kb and is highly expressed in human adult brain tissue (FIG. 6A). Interestingly, RR/B mRNA is expressed with about 50-fold greater abundance in human fetal brain tissue relative to human adult brain tissue or any other tissue analyzed. A low level of RR/B mRNA expression was found in adult pancreatic tissue, and a low level of RR/B mRNA expression was found in fetal kidney (FIG. 6B). RR/B mRNA was also detectable in brain cell lines of glioblastoma (U373 cell line) and neuroblastoma (SK-N-SH cell line) origin (FIG. 7), as well as in megakaryocytice cell lines (FIG. 8A). RR/B mRNA was not detected in various non-hematopoietic cell lines (FIGS. 8A and 8B).

Figure 9:
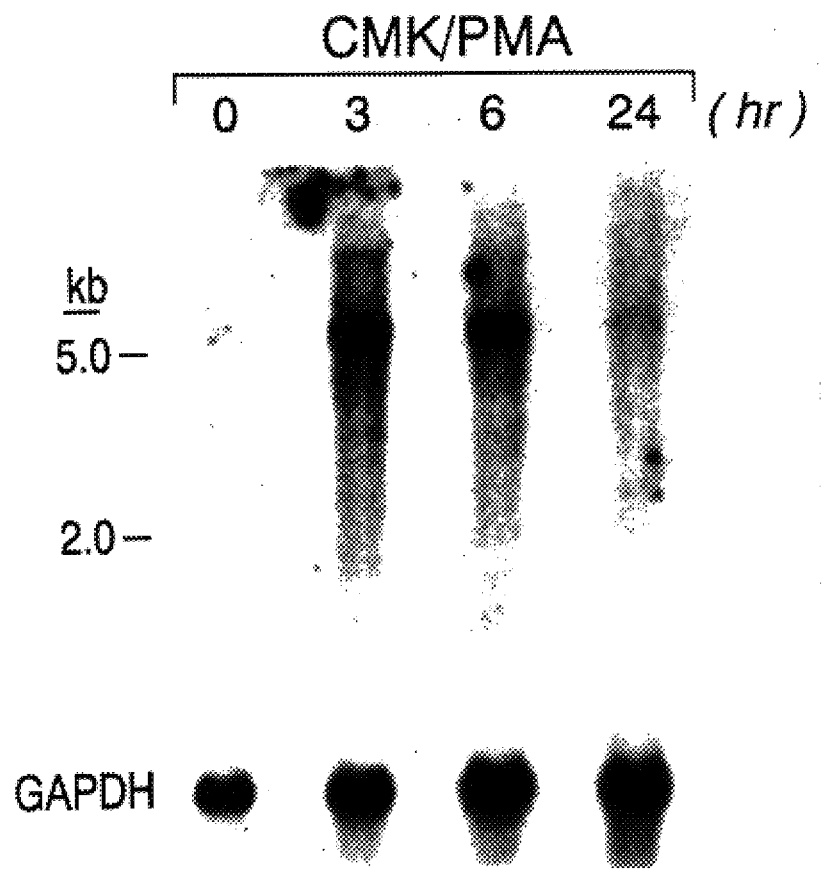
FIG. 9 is a Northern blot of human RR/B mRNA in the presence of PMA in permanent CMK cell line.

Expression of RR/B was found to be upregulated by PMA (phorbol 12-myristate 13-acetate) (FIG. 9). Kinetic analysis of RR/B expression in CMK megakaryocytic cell lines induced to differentiate in vitro by PMA for 3, 6, or 24 hr, revealed upregulation of RR/B expression after 3 hr and 6 hr followed by downregulation of RR/B after 24 hr.

Northern Blot Analysis.

Poly (A)<+> mRNA samples (usually 2 micrograms) were fractionated by electrophoresis on 1.5 percent agarose gels in the presence of 1 molar formaldehyde as described in Rave et al., Nucleic Acids Res., 6, 3559–3567 (1979) and transferred to nitrocellulose as described in Thomas P. S., Proc. Natl. Acad. Sci. USA, 77, 5201–5205 (1980). The blots were prehybridized overnight at 42 degrees C. in 50 percent formamide, 0.75 molar NaCl, 25 millimolar PIPES [1, 4-piperazine-bis-(2-ethanesulfonic acid)], pH 6.8, 0.2 percent sodium dodecyl sulfate (SDS), 25 millimolar EDTA, 100 micrograms per milliliter salmon sperm DNA, 100 micrograms per milliliter yeast mRNA and 5× Denhardt's solution as described in Denhardt, D., Biochem. Biophys. Res. Comm., 23, 641–646 (1966). The blots were then hybridized overnight with $^{32}$P-labeled probes at 42 degrees C. in the same medium but the 1× Denhardt's solution.

One-quarter or one-eighth of each crude plasmid extract or (for followup screening) 100 nanograms of purified super-coiled plasmid were labeled with $^{32}$P by random primed as described in Feinberg, et al., Anal. Biochem. 132:6–13 (1983) to specific activities of 2–4×10$^8$ counts per minute per microgram. Blots were washed in two changes of 2× SSC standard sodium citrate solution; 30 millimoles trisodium citrate and 0.3 molar sodium chloride at pH 7.0) 0.2 percent SDS for 60 minutes each at 42 degrees C. and once in 0.1× percent SSC (1.5 millimolar trisodium citrate and 15 millimolar sodium chloride at pH 7.0), 0.2 percent SDS for 15 minutes at 67 degrees C. The washed blots were then exposed to Kodak XRP-5 or XAR-1 X-ray film at minus 50 degrees C. using Cronex Lightening Plus intensification screens for 1 hr. to 4 days. Size estimates were based on comparisons with plasmid λ-HindIII standards.

EXAMPLE V

Antigenic Peptides.

Two 13-residue synthetic polypeptides corresponding to two amino acid residue sequences within the RR/B open reading frame were chemically synthesized to aid in detection of RR/B.

Other synthetic polypeptides of the invention will be useful as antigenic peptides for generation of antibodies specific for RR/B provided they possess the following characteristics. The peptide will include a minimum of 12 and preferably 15 amino acid residues, and an optimum length of 20–21 amino acids. The hydrophilicity and antigenic index of the amino acid sequence of RR/B may be determined by Analytical Biotechnology Sciences, Boston, Mass., using computer programming. For example, additional potential synthetic peptides useful according to the invention include the group comprising amino acid residues 294–307, 175–186, 351–371 and 412–429 of FIG. 1B (SEQ ID NO: 2).

The amino acid sequences of the polypeptides were searched in a computer database to preclude the possibility that at reasonable concentrations, antisera to any of these polypeptides would specifically interact with any protein of a known sequence. Neither of the polypeptides were found to have a close homolog.

Antisera to the polypeptide-carrier conjugates were raised in rabbits. The sera were shown to react strongly with the appropriate polypeptides by ELISA following the procedures of Green et al., Cell, 28, 477–487 (1982).

The antisera may then be used to probe extracts of $^{35}$S-methionine labeled cells, as described below. Antisera to synthetic polypeptides P1 and P2 were found to react with a protein with a gel mobility of about 60K daltons.

The amino acid residue sequence of synthetic polypeptides P1 and P2 are as represented by the formulas below, from left to right and in the direction from amino-terminus to carboxy-terminus, using conventional single letter code for amino acid residues:

EXAMPLE VI

Preparation of Antibodies.

The peptide ABCP-51 (P1) corresponding to amino acid residues 198 to 210 and ABCP-52 (P2) corresponding to amino acid residues 258 to 270 for the human and mouse RR-B proteins were synthesized. Coupling of the peptide to carrier protein and immunizations was performed as described (Dymecki, S. M., supra). Rabbit antibodies against this peptide were raised and sera were titered against peptide antigen by ELISA. The sera exhibiting the highest titer (1:27,000) were used in subsequent experiments.

Techniques for preparing monoclonal antibodies are well known, and monoclonal antibodies of this invention may be prepared by using the synthetic polypeptides of this invention, preferably bound to a carrier, as the immunogen as was done by Arnheiter et al., Nature, 294, 278–280 (1981).

Monoclonal antibodies are typically obtained from hybridoma tissue cultures or from ascites fluid obtained from animals into which the hybridoma tissue was introduced. Nevertheless, monoclonal antibodies may be described as being "raised to" or "induced by" the synthetic polypeptides of this invention or their conjugates with a carrier.

Antibodies are utilized along with an "indicating group" also sometimes referred to as a "label". The indicating group or label is utilized in conjunction with the antibody as a means for determining whether an immune reaction has taken place, and in some instances for determining the extent of such a reaction.

The indicating group may be a single atom as in the case of radioactive elements such as iodine 125 or 131, hydrogen 3 or sulfur 35, or NMR-active elements such as fluorine 19 or nitrogen 15. The indicating group may also be a molecule such as a fluorescent dye like fluorescein, or an enzyme, such as horseradish peroxidase (HRP), or the like.

The terms "indicating group" or "label" are used herein to include single atoms and molecules that are linked to the antibody or used separately, and whether those atoms or molecules are used alone or in conjunction with additional reagents. Such indicating groups or labels are themselves well-known in immunochemistry and constitute a part of this invention only insofar as they are utilized with otherwise novel antibodies, methods and/or systems.

EXAMPLE VII

Detection of RR/B and Subcellular Localization.

Another embodiment of this invention relates to an assay for the presence of RR/B. Here, an above-described antibody is raised and harvested. The antibody or idiotype-containing polyamide portion thereof is then admixed with candidate tissue and an indicating group. The presence of the naturally occurring amino acid sequence is ascertained by the formation of an immune reaction as signaled by the indicating group. Candidate tissues include any tissue or cell line or bodily fluid to be tested for the presence of RR/B.

The expression of the RR-B gene product was investigated using and antiserum prepared in rabbits against two peptides as described above.

The CMK cells or U3T3 cells were metabolically labeled with $^{35}$S-methionine and extracts were immunoprecipitated with anti-RR-B antiserum. A major protein species of 60 kd was detected in CMK and U3T3 cells. RR-B protein was localized in the membrane with some of the protein found in the cytoplasm, by Western blot analysis of the nuclear membrane and cytoplasmic fractions, as generally described in Towbin et al., Proc. Natl. Acad. Sci. USA, 76, 4350–4354 (1979). This localization for RR-B was confirmed by immunofluorescence analysis to be associated mainly with the plasma membrane.

Metabolic labeling immunoprecipitation, and immunolocalization assays were performed in CMK and U373 cells as described previously (Furth, M. E., et al., Oncogene 1:47–58, 1987; Laemmli, U. K., Nature 227:680–685, 1970; Yarden, Y., et al., EMBO J. 6:3341–3351, 1987; Konopka, J. B., et al., Mol. Cell. Biol. 5:3116–3123, 1985). For immunoblot analysis, total lysates were prepared (using Fruth's lysis buffer) (Fruth, M. E., et al., Oncogene, 1:47–58, 1987). Relative protein concentrations were determined with a calorimetric assay kit (Bio-Rad) with bovine serum albumin as the standard. A protein of lysate containing approximately 0.05 mg of protein was mixed with an equal volume of 2× SDS sample buffer containing 2 mercaptoethanol, boiled for 5 min., fractioned on 10% polyacrylamide-SDS gels (Konopka, J. B., et al., J. Virol., 51:223–232, 1984) and transferred to immunobilon polyvinyldine difluoride (Millipore Corp., Bedford, Mass.) filters. Protein blots were treated with specific antipeptide antibodies (see below). Primary binding of the RR-B- specific antibodies was detected using anti-IgG second antibodies conjugated to horseradish peroxidase and subsequent chemiluminescence development ECL Western blotting system (Amersham International).

For metabolic labeling, $10^6$ cells were labeled with 100 $\mu$Ci of $^{35}$S-methionine in 1 ml of Dulbecco's modified Eagles medium minus methionine (Amersham Corp.) for 16 h. Immunoprecipitation of RR-B protein form labeled cells with antipeptide antiserum was performed as described (Dymecki, S. M., et al., J. Biol. Chem 267:4815–4823, 1992). Portions of lysates containing $10^7$ cpm of acid-insoluble $^{35}$S-methionine were incubated with 1 $\mu$g of the antiserum in 0.5 ml of reaction mixture. Immunoprecipitation samples were analyzed by SDS-polylarcylamide gel electrophoresis and autoradiography.

For immunolocalization studies, $10^7$ CMK cells were resuspended in 1 ml of sonication buffer (60 mM Tris-HCl, pH 7.5, 6 mM EDTA, 15 mM EGTA, 0.75M sucrose, 0.03% leupeptin 12 mM phenylmethylsulfonyl fluoride, 30 mM 2-mercaptoethanol). Cells were sonicated 6 times for 10 seconds each and centrifuged at 25,000×g for 10 min at 4° C. The pellet was dissolved in 1 ml of sonication buffer and centrifuged at 25,000×g for 10 min at 4° C.

The pellet (nucleus fraction) was resuspended in 1 ml of sonication buffer and added to an equal volume of 2× SDS sample buffer. The supernatant obtained above (after the first sonication) was again centrifuged at 100,000×g for 40 min at 4° C. The supernatant (cytosolic fraction) was removed and added to an equal volume of 2× concentrated SDS sample buffer. The remaining pellet (membrane fraction) was washed and dissolved in sonication buffer and SDS sample buffer as described above. Protein samples were analyzed by electrophoresis on 10% polyacrylamide gels, according to the Laemmli method (Konopka, J. B., supra). The proteins were transferred from the gels on a 0.45-$\mu$m plyvinylidine difluoride membrane for subsequent immunoblot analysis. Primary binding of the RR-B specific antibodies was detected using anti-IgG second antibodies conjugated to horseradish peroxidase.

For immunohistochemical localization of RR-B protein, CMK cells or U3T3 were grown on cover slips to approximately 50% confluence and were washed with PBS (pH 7.4) after removing the medium. The cells were prefixed for 1 min at 37° C. in 1% paraformaldehyde containing 0.075% Triton X-100, rinsed with PBS and then fixed for 10 min with 4% paraformaldehyde. After the fixation step, cells were rinsed in PBS, quenched in PBS with 0.1 and finally rinsed again in PBS. For antibody staining, the cells were first blocked with a blocking solution (3% bovine serum albumin in PBS) and incubated for 1 h at 37° C. The cells were then incubated for 1 h at 37° C. with antiserum (1:100 dilution or with preimmune rabbit serum (1:100) (see below). After the incubation with the primary antibody, the cells were washed in PBS containing 3% bovine and serum albumin and 0.1% Tween 20 and incubated for 1 h at 37° C. in fluorescein-conjugated donkey anti-rabbit IgGs (Jackson Immunoresearch, Maine) diluted 1:100 in blocking solution.

The coverslips were washed in PBS (pH 8.0), and glycerol was added to each coverslip before mounting on glass slides and sealing with clear nail polish. All glass slides were examined with a Zeiss Axiophot microscope.

EXAMPLE VIII

The above methods for detection of RR/B protein or nucleic acid are applicable to analyses involving tissues, cell lines and bodily fluids suspected of containing the RR/B marker.

For example, a sample of brain tissue suspected of possessing neoplastic properties may be analyzed. Neoplastic tissue typically contains lower levels of RR/B relative to non-neoplastic tissue.

An aliquot of the suspect sample and a non-neoplastic control sample are provided and admixed with an effective amount of an antibody specific for RR/B, as herein described, and an indicating group. The admixture is typically incubated, as is known, for a time sufficient to permit an immune reaction to occur. The incubated admixture is then assayed for the presence of an immune reaction as indicated by the indicating group. The relative levels of RR/B in the suspect sample and the control sample are then compared, allowing for diagnosis of a neoplastic or non-neoplastic state in the suspect sample.

Alternatively, where RR/B is a normal constituent of a tissue, e.g., human brain tissue, detection of RR/B may be used to determine the neural or non-neural origin of the tissue. In this respect, the level of RR/B is measured in a suspect tissue and compared to the amount present relative to human brain tissue. A comparable level of RR/B will indicate neural origin of the suspect tissue, whereas a relatively low level of RR/B in the suspect tissue will usually indicate that the suspect tissue is of non-neural origin.

The above types of analyses for the presence of RR/B may, of course, be performed using analysis for RR/B mRNA, e.g., via Northern blot or RNA dot blot analyses, both of which are conventional and known in the art.

A diagnostic system, preferably in kit form, comprises yet another embodiment of this invention. This system is useful for assaying the presence of RR/B or its derivative in brain cells by the formation of an immune complex. This system includes at least one package that contains an antibody of this invention.

An indicating group or label is preferably supplied along with the antibody and may be packaged therewith or packaged separately. Additional reagents such as hydrogen peroxide and diaminobenzideine may also be included in the system when an indicating group such as HRP is utilized. Such materials are readily available in commerce, as are many indicating groups, and need not be supplied along with the diagnostic system. In addition, some reagents such as hydrogen peroxide decompose on standing, or are otherwise short-lived like some radioactive elements, and are better supplied by the end-user.

OTHER EMBODIMENTS

Other embodiments will be evident to those of skill in the art. It should be understood that the foregoing detailed description is provided for clarity only and is merely exemplary. The spirit and scope of the present invention are not limited thereto, being defined by the claims set forth below.

We claim:

1. A monoclonal antibody specific for an epitope of RR/B, said RR/B comprising the amnino acid sequence presented in SEQ ID NO: 2.

2. The monoclonal antibody of claim 1, comprising an antibody specific for an epitope specified by the amnino acid residues 198 to 210 (S-S-E-E-L-E-T-E-D-E-R-L-V) of SEQ ID NO: 2.

3. The monoclonal antibody of claim 1, comprising an antibody specific for an epitope specified by the amino acid residues 258 to 270 (K-Q-R-K-S-K-E-I-V-E-E-A-I) of SEQ ID NO: 2.

4. A method of assaying for the presence of RR/B in a sample of mammalian cells, comprising the steps of:

(a) providing an antibody specific for an epitope of said RR/B; and (b) assaying for the presence of said RR/B by admixing an aliquot from a sample of said mammalian cells with said antibody under conditions sufficient to allow for formation and detection of an immune complex of said RR/B and said antibody.

5. The method of claim 4 wherein said epitope comprises an amino acid sequence selected from the group consisting of: amino acid residues 198 to 210 (S-S-E-E-L-E-T-E-D-E-R-L-V) and amino acid residues 258 to 270 (K-Q-R-K-S-K-E-I-V-E-E-A-I) of SEQ ID NO: 2.

* * * * *

UNITED STATES PATENT AND TRADEMARK OFFICE
CERTIFICATE OF CORRECTION

PATENT NO. : 5,863,744
DATED : January 26, 1999
INVENTOR(S) : Avraham et al.

It is certified that error appears in the above-identified patent and that said Letters Patent is hereby corrected as shown below:

Column 5, line 11, replace "cell—cell" with --cell-cell--.

Column 6, line 21, replace "cell—cell" with --cell-cell--.

Column 6, line 57, replace "cell—cell" with --cell-cell--.

Column 6, line 61, replace "cell—cell" with --cell-cell--.

Column 7, line 3, replace "cell—cell" with --cell-cell--.

Signed and Sealed this

Sixth Day of June, 2000

Attest:

Q. TODD DICKINSON

*Attesting Officer*   *Director of Patents and Trademarks*

UNITED STATES PATENT AND TRADEMARK OFFICE
CERTIFICATE OF CORRECTION

PATENT NO. : 5,863,744
DATED : January 26, 1999
INVENTOR(S) : Avraham, et. al.

It is certified that error appears in the above-identified patent and that said Letters Patent is hereby corrected as shown below:

Title page, item [73], Assignee: replace "New England Deaconess Hospital Corporation" with --Beth Israel Deaconess Medical Center, Inc.--

Signed and Sealed this

Twenty-second Day of August, 2000

Attest:

Q. TODD DICKINSON

*Attesting Officer*　　　　　　　　*Director of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1770 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..1767

( x i ) SEQUENCE DESCRIPTION: SEQ ID NO:1:

```
ATG  TCA  GTC  AGT  GTG  CAT  GAG  AAC  CGC  AAG  TCC  AGG  GCC  AGC  AGC  GGC         48
Met  Ser  Val  Ser  Val  His  Glu  Asn  Arg  Lys  Ser  Arg  Ala  Ser  Ser  Gly
 1              Ser       5                        10                      15

TCC  ATT  AAC  ATC  TAT  CTG  TTT  CAC  AAG  TCC  TCC  TAC  GCT  GAC  AGC  GTC         96
Ser  Ile  Asn  Ile  Tyr  Leu  Phe  His  Lys  Ser  Ser  Tyr  Ala  Asp  Ser  Val
                20                       25                      30

CTC  ACT  CAC  CTG  AAT  CTT  TTA  CGC  CAG  CAG  CGT  CTC  TTC  ACT  GAC  GTC        144
Leu  Thr  His  Leu  Asn  Leu  Leu  Arg  Gln  Gln  Arg  Leu  Phe  Thr  Asp  Val
          35                         40                      45

CTT  CTC  CAT  GCC  GGA  AAT  AGG  ACC  TTC  CCT  TGC  CAC  CGG  GCA  GTG  CTG        192
Leu  Leu  His  Ala  Gly  Asn  Arg  Thr  Phe  Pro  Cys  His  Arg  Ala  Val  Leu
     50                            55                   60

GCT  GCA  TGC  AGT  CGC  TAC  TTT  GAG  GCC  ATG  TTC  AGT  GGT  GGC  CTG  AAA        240
Ala  Ala  Cys  Ser  Arg  Tyr  Phe  Glu  Ala  Met  Phe  Ser  Gly  Gly  Leu  Lys
 65                       70                         75                      80

GAG  AGC  CAG  GAC  AGT  GAG  GTC  AAC  TTT  GAC  AAT  TCC  ATC  CAC  CCA  GAA        288
Glu  Ser  Gln  Asp  Ser  Glu  Val  Asn  Phe  Asp  Asn  Ser  Ile  His  Pro  Glu
                    85                       90                      95

GTC  TTG  GAG  CTG  CTG  CTT  GAC  TAT  GCG  TAC  TCC  TCC  CGG  GTC  ATC  ATC        336
Val  Leu  Glu  Leu  Leu  Leu  Asp  Tyr  Ala  Tyr  Ser  Ser  Arg  Val  Ile  Ile
              100                      105                     110
```

-continued

| | | | | | | | | | | | | | | | | |
|---|---|---|---|---|---|---|---|---|---|---|---|---|---|---|---|---|
| AAT | GAA | GAA | AAT | GCA | GAA | TCG | CTC | CTG | GAA | GCT | GGT | GAC | ATG | CTG | GAG | 384 |
| Asn | Glu | Glu 115 | Asn | Ala | Glu | Ser 120 | Leu | Leu | Glu | Ala | Gly 125 | Asp | Met | Leu | Glu | |
| TTT | CAA | GAC | ATC | CGG | GAT | GCA | TGT | GCA | GAG | TTC | CTG | GAA | AAG | AAC | CTG | 432 |
| Phe | Gln 130 | Asp | Ile | Arg | Asp | Ala 135 | Cys | Ala | Glu | Phe | Leu 140 | Glu | Lys | Asn | Leu | |
| CAT | CCC | ACC | AAC | TGC | CTG | GGC | ATG | CTG | CTG | CTG | TCT | GAT | GCA | CAC | CAG | 480 |
| His 145 | Pro | Thr | Asn | Cys | Leu 150 | Gly | Met | Leu | Leu | Leu 155 | Ser | Asp | Ala | His | Gln 160 | |
| TGC | ACC | AAG | CTG | TAC | GAA | CTA | TCT | TGG | AGA | ATG | TGT | CTC | AGC | AAC | TTC | 528 |
| Cys | Thr | Lys | Leu | Tyr 165 | Glu | Leu | Ser | Trp | Arg 170 | Met | Cys | Leu | Ser | Asn 175 | Phe | |
| CAA | ACC | ATC | AGG | AAG | AAT | GAA | GAT | TTC | CTC | CAG | CTG | CCC | CAG | GAC | ATG | 576 |
| Gln | Thr | Ile | Arg 180 | Lys | Asn | Glu | Asp | Phe 185 | Leu | Gln | Leu | Pro | Gln 190 | Asp | Met | |
| GTA | GTG | CAA | CTC | TTG | TCC | AGT | GAA | GAG | CTG | GAG | ACA | GAG | GAT | GAA | AGG | 624 |
| Val | Val | Gln 195 | Leu | Leu | Ser | Ser | Glu 200 | Glu | Leu | Glu | Thr | Glu 205 | Asp | Glu | Arg | |
| CTT | GTG | TAC | GAG | TCT | GCA | ATT | AAC | TGG | ATC | AGC | TAT | GAC | CTG | AAG | AAG | 672 |
| Leu | Val | Tyr 210 | Glu | Ser | Ala | Ile | Asn 215 | Trp | Ile | Ser | Tyr | Asp 220 | Leu | Lys | Lys | |
| CGC | TAT | TGC | TAC | CTC | CCA | GAA | CTG | TTG | CAG | ACA | GTA | AGG | CTG | GCA | CTT | 720 |
| Arg | Tyr | Cys 225 | Tyr | Leu | Pro | Glu 230 | Leu | Leu | Gln | Thr 235 | Val | Arg | Leu | Ala | Leu 240 | |
| CTG | CCA | GCC | ATC | TAT | CTC | ATG | GAG | AAT | GTG | GCC | ATG | GAG | GAA | CTC | ATC | 768 |
| Leu | Pro | Ala | Ile | Tyr 245 | Leu | Met | Glu | Asn | Val 250 | Ala | Met | Glu | Glu | Leu 255 | Ile | |
| ACC | AAG | CAG | AGA | AAG | AGT | AAG | GAA | ATT | GTG | GAA | GAG | GCC | ATC | AGG | TGC | 816 |
| Thr | Lys | Gln | Arg 260 | Lys | Ser | Lys | Glu | Ile 265 | Val | Glu | Glu | Ala | Ile 270 | Arg | Cys | |
| AAA | CTG | AAA | ATC | CTG | CAG | AAT | GAC | GGT | GTG | GTA | ACC | AGC | CTC | TGT | GCC | 864 |
| Lys | Leu | Lys 275 | Ile | Leu | Gln | Asn | Asp 280 | Gly | Val | Val | Thr | Ser 285 | Leu | Cys | Ala | |
| CGA | CCT | CGG | AAA | ACT | GGC | CAT | GCC | CTC | TTC | CTT | CTG | GGA | GGA | CAG | ACT | 912 |
| Arg | Pro 290 | Arg | Lys | Thr | Gly | His 295 | Ala | Leu | Phe | Leu | Leu 300 | Gly | Gly | Gln | Thr | |
| TTC | ATG | TGT | GAC | AAG | TTG | TAT | CTG | GTA | GAC | CAG | AAG | GCC | AAA | GAA | ATC | 960 |
| Phe 305 | Met | Cys | Asp | Lys | Leu 310 | Tyr | Leu | Val | Asp | Gln 315 | Lys | Ala | Lys | Glu | Ile 320 | |
| ATT | CCC | AAG | GCT | GAC | ATT | CCC | AGC | CCA | AGA | AAA | GAG | TTT | AGT | GCA | TGT | 1008 |
| Ile | Pro | Lys | Ala | Asp 325 | Ile | Pro | Ser | Pro | Arg 330 | Lys | Glu | Phe | Ser | Ala 335 | Cys | |
| GCG | ATT | GGC | TGC | AAA | GTG | TAC | ATT | ACT | GGG | GGG | CGG | GGG | TCT | GAA | AAT | 1056 |
| Ala | Ile | Gly | Cys 340 | Lys | Val | Tyr | Ile | Thr 345 | Gly | Gly | Arg | Gly | Ser 350 | Glu | Asn | |
| GGG | GTC | TCG | AAA | GAT | GTC | TGG | GTT | TAT | GAT | ACC | CTG | CAC | GAG | GAG | TGG | 1104 |
| Gly | Val | Ser 355 | Lys | Asp | Val | Trp | Val 360 | Tyr | Asp | Thr | Leu | His 365 | Glu | Glu | Trp | |
| TCC | AAG | GCT | GCC | CCC | ATG | CTG | GTG | GCC | AGG | TTT | GGC | CAT | GGC | TCT | GCT | 1152 |
| Ser | Lys 370 | Ala | Ala | Pro | Met | Leu 375 | Val | Ala | Arg | Phe | Gly 380 | His | Gly | Ser | Ala | |
| GAA | CTG | AAG | CAC | TGC | CTG | TAT | GTG | GTT | GGG | GGG | CAC | ACG | GCC | GCA | ACT | 1200 |
| Glu | Leu | Lys | His 385 | Cys | Leu | Tyr 390 | Val | Val | Gly | Gly | His 395 | Thr | Ala | Ala | Thr 400 | |
| GGC | TGC | CTC | CCG | GCC | TCC | CCC | TCA | GTC | TCT | CTA | AAG | CAG | GTA | GAA | CAT | 1248 |
| Gly | Cys | Leu | Pro | Ala 405 | Ser | Pro | Ser | Val | Ser 410 | Leu | Lys | Gln | Val | Glu 415 | His | |
| TAT | GAC | CCC | ACA | ATC | AAC | AAA | TGG | ACC | ATG | GTG | GCC | CCA | CTC | CGA | GAA | 1296 |
| Tyr | Asp | Pro | Thr 420 | Ile | Asn | Lys | Trp | Thr 425 | Met | Val | Ala | Pro | Leu 430 | Arg | Glu | |

| | | | | | | | | | | | | | | | | |
|---|---|---|---|---|---|---|---|---|---|---|---|---|---|---|---|---|
| GGC | GTT | AGC | AAC | GCC | GCA | GTA | GTG | AGT | GCC | AAA | CTT | AAG | TTA | TTT | GCT | 1344 |
| Gly | Val | Ser | Asn | Ala | Ala | Val | Val | Ser | Ala | Lys | Leu | Lys | Leu | Phe | Ala | |
| | | 435 | | | | 440 | | | | | 445 | | | | | |
| TTC | GGA | GGT | ACC | AGT | GTC | AGT | CAT | GAC | AAG | CTC | CCC | AAA | GTT | CAG | TGT | 1392 |
| Phe | Gly | Gly | Thr | Ser | Val | Ser | His | Asp | Lys | Leu | Pro | Lys | Val | Gln | Cys | |
| | 450 | | | | | 455 | | | | | 460 | | | | | |
| TAC | GAT | CAG | TGT | GAA | AAC | AGG | TGG | ACT | GTA | CCG | GCC | ACC | TGT | CCC | CAG | 1440 |
| Tyr | Asp | Gln | Cys | Glu | Asn | Arg | Trp | Thr | Val | Pro | Ala | Thr | Cys | Pro | Gln | |
| 465 | | | | | 470 | | | | | 475 | | | | | 480 | |
| CCC | TGG | CGT | TAC | ACA | GCA | GCA | GCT | GTG | CTG | GGG | AAC | CAG | ATT | TTT | ATT | 1488 |
| Pro | Trp | Arg | Tyr | Thr | Ala | Ala | Ala | Val | Leu | Gly | Asn | Gln | Ile | Phe | Ile | |
| | | | | 485 | | | | | 490 | | | | | 495 | | |
| ATG | GGG | GGT | GAT | ACA | GAA | TTC | TCT | GCC | TGC | TCT | GCT | TAT | AAA | TTC | AAC | 1536 |
| Met | Gly | Gly | Asp | Thr | Glu | Phe | Ser | Ala | Cys | Ser | Ala | Tyr | Lys | Phe | Asn | |
| | | | 500 | | | | | 505 | | | | | 510 | | | |
| AGT | GAG | ACT | TAC | CAG | TGG | ACC | AAA | GTG | GGA | GAT | GTG | ACA | GCA | AAG | CGC | 1584 |
| Ser | Glu | Thr | Tyr | Gln | Trp | Thr | Lys | Val | Gly | Asp | Val | Thr | Ala | Lys | Arg | |
| | | 515 | | | | | 520 | | | | | 525 | | | | |
| ATG | AGC | TGC | CAT | GCT | GTG | GCC | TCT | GGA | AAC | AAA | CTC | TAC | GTG | GTT | GGA | 1632 |
| Met | Ser | Cys | His | Ala | Val | Ala | Ser | Gly | Asn | Lys | Leu | Tyr | Val | Val | Gly | |
| | 530 | | | | | 535 | | | | | 540 | | | | | |
| GGA | TAC | TTT | GGC | ATT | CAG | CGA | TGC | AAG | ACT | TTG | GAC | TGC | TAC | GAT | CCA | 1680 |
| Gly | Tyr | Phe | Gly | Ile | Gln | Arg | Cys | Lys | Thr | Leu | Asp | Cys | Tyr | Asp | Pro | |
| 545 | | | | | 550 | | | | | 555 | | | | | 560 | |
| ACA | TTA | GAC | GTG | TGG | AAC | AGC | ATC | ACC | ACT | GTC | CCG | TAC | TCG | CTG | ATT | 1728 |
| Thr | Leu | Asp | Val | Trp | Asn | Ser | Ile | Thr | Thr | Val | Pro | Tyr | Ser | Leu | Ile | |
| | | | | 565 | | | | | 570 | | | | | 575 | | |
| CCT | ACT | GCA | TTT | GTC | AGC | ACC | TGG | AAA | CAT | CTG | CCT | TCT | TAA | | | 1770 |
| Pro | Thr | Ala | Phe | Val | Ser | Thr | Trp | Lys | His | Leu | Pro | Ser | | | | |
| | | | 580 | | | | | 585 | | | | | | | | |

(2) INFORMATION FOR SEQ ID NO:2:

(i) SEQUENCE CHARACTERISTICS:
        (A) LENGTH: 589 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Ser | Val | Ser | Val | His | Glu | Asn | Arg | Lys | Ser | Arg | Ala | Ser | Ser | Gly |
| 1 | | | | 5 | | | | | 10 | | | | | 15 | |
| Ser | Ile | Asn | Ile | Tyr | Leu | Phe | His | Lys | Ser | Ser | Tyr | Ala | Asp | Ser | Val |
| | | | 20 | | | | | 25 | | | | | 30 | | |
| Leu | Thr | His | Leu | Asn | Leu | Leu | Arg | Gln | Gln | Arg | Leu | Phe | Thr | Asp | Val |
| | | 35 | | | | | 40 | | | | | 45 | | | |
| Leu | Leu | His | Ala | Gly | Asn | Arg | Thr | Phe | Pro | Cys | His | Arg | Ala | Val | Leu |
| | 50 | | | | | 55 | | | | | 60 | | | | |
| Ala | Ala | Cys | Ser | Arg | Tyr | Phe | Glu | Ala | Met | Phe | Ser | Gly | Gly | Leu | Lys |
| 65 | | | | | 70 | | | | | 75 | | | | | 80 |
| Glu | Ser | Gln | Asp | Ser | Glu | Val | Asn | Phe | Asp | Asn | Ser | Ile | His | Pro | Glu |
| | | | | 85 | | | | | 90 | | | | | 95 | |
| Val | Leu | Glu | Leu | Leu | Leu | Asp | Tyr | Ala | Tyr | Ser | Ser | Arg | Val | Ile | Ile |
| | | | 100 | | | | | 105 | | | | | 110 | | |
| Asn | Glu | Glu | Asn | Ala | Glu | Ser | Leu | Leu | Glu | Ala | Gly | Asp | Met | Leu | Glu |
| | | 115 | | | | | 120 | | | | | 125 | | | |
| Phe | Gln | Asp | Ile | Arg | Asp | Ala | Cys | Ala | Glu | Phe | Leu | Glu | Lys | Asn | Leu |
| | 130 | | | | | 135 | | | | | 140 | | | | |

-continued

| | | | | | | | | | | | | | | | |
|---|---|---|---|---|---|---|---|---|---|---|---|---|---|---|---|
| His | Pro | Thr | Asn | Cys | Leu | Gly | Met | Leu | Leu | Leu | Ser | Asp | Ala | His | Gln |
| 145 | | | | 150 | | | | | 155 | | | | | | 160 |
| Cys | Thr | Lys | Leu | Tyr | Glu | Leu | Ser | Trp | Arg | Met | Cys | Leu | Ser | Asn | Phe |
| | | | | 165 | | | | | 170 | | | | | 175 | |
| Gln | Thr | Ile | Arg | Lys | Asn | Glu | Asp | Phe | Leu | Gln | Leu | Pro | Gln | Asp | Met |
| | | | 180 | | | | | 185 | | | | | 190 | | |
| Val | Val | Gln | Leu | Leu | Ser | Ser | Glu | Glu | Leu | Glu | Thr | Glu | Asp | Glu | Arg |
| | | 195 | | | | | 200 | | | | | 205 | | | |
| Leu | Val | Tyr | Glu | Ser | Ala | Ile | Asn | Trp | Ile | Ser | Tyr | Asp | Leu | Lys | Lys |
| | 210 | | | | | 215 | | | | | 220 | | | | |
| Arg | Tyr | Cys | Tyr | Leu | Pro | Glu | Leu | Leu | Gln | Thr | Val | Arg | Leu | Ala | Leu |
| 225 | | | | | 230 | | | | | 235 | | | | | 240 |
| Leu | Pro | Ala | Ile | Tyr | Leu | Met | Glu | Asn | Val | Ala | Met | Glu | Glu | Leu | Ile |
| | | | | 245 | | | | | 250 | | | | | 255 | |
| Thr | Lys | Gln | Arg | Lys | Ser | Lys | Glu | Ile | Val | Glu | Glu | Ala | Ile | Arg | Cys |
| | | | 260 | | | | | 265 | | | | | 270 | | |
| Lys | Leu | Lys | Ile | Leu | Gln | Asn | Asp | Gly | Val | Val | Thr | Ser | Leu | Cys | Ala |
| | | 275 | | | | | 280 | | | | | 285 | | | |
| Arg | Pro | Arg | Lys | Thr | Gly | His | Ala | Leu | Phe | Leu | Leu | Gly | Gly | Gln | Thr |
| | 290 | | | | | 295 | | | | | 300 | | | | |
| Phe | Met | Cys | Asp | Lys | Leu | Tyr | Leu | Val | Asp | Gln | Lys | Ala | Lys | Glu | Ile |
| 305 | | | | | 310 | | | | | 315 | | | | | 320 |
| Ile | Pro | Lys | Ala | Asp | Ile | Pro | Ser | Pro | Arg | Lys | Glu | Phe | Ser | Ala | Cys |
| | | | | 325 | | | | | 330 | | | | | 335 | |
| Ala | Ile | Gly | Cys | Lys | Val | Tyr | Ile | Thr | Gly | Gly | Arg | Gly | Ser | Glu | Asn |
| | | | 340 | | | | | 345 | | | | | 350 | | |
| Gly | Val | Ser | Lys | Asp | Val | Trp | Val | Tyr | Asp | Thr | Leu | His | Glu | Glu | Trp |
| | | 355 | | | | | 360 | | | | | 365 | | | |
| Ser | Lys | Ala | Ala | Pro | Met | Leu | Val | Ala | Arg | Phe | Gly | His | Gly | Ser | Ala |
| | 370 | | | | | 375 | | | | | 380 | | | | |
| Glu | Leu | Lys | His | Cys | Leu | Tyr | Val | Val | Gly | Gly | His | Thr | Ala | Ala | Thr |
| 385 | | | | | 390 | | | | | 395 | | | | | 400 |
| Gly | Cys | Leu | Pro | Ala | Ser | Pro | Ser | Val | Ser | Leu | Lys | Gln | Val | Glu | His |
| | | | | 405 | | | | | 410 | | | | | 415 | |
| Tyr | Asp | Pro | Thr | Ile | Asn | Lys | Trp | Thr | Met | Val | Ala | Pro | Leu | Arg | Glu |
| | | | 420 | | | | | 425 | | | | | 430 | | |
| Gly | Val | Ser | Asn | Ala | Ala | Val | Val | Ser | Ala | Lys | Leu | Lys | Leu | Phe | Ala |
| | | 435 | | | | | 440 | | | | | 445 | | | |
| Phe | Gly | Gly | Thr | Ser | Val | Ser | His | Asp | Lys | Leu | Pro | Lys | Val | Gln | Cys |
| | 450 | | | | | 455 | | | | | 460 | | | | |
| Tyr | Asp | Gln | Cys | Glu | Asn | Arg | Trp | Thr | Val | Pro | Ala | Thr | Cys | Pro | Gln |
| 465 | | | | | 470 | | | | | 475 | | | | | 480 |
| Pro | Trp | Arg | Tyr | Thr | Ala | Ala | Ala | Val | Leu | Gly | Asn | Gln | Ile | Phe | Ile |
| | | | | 485 | | | | | 490 | | | | | 495 | |
| Met | Gly | Gly | Asp | Thr | Glu | Phe | Ser | Ala | Cys | Ser | Ala | Tyr | Lys | Phe | Asn |
| | | | 500 | | | | | 505 | | | | | 510 | | |
| Ser | Glu | Thr | Tyr | Gln | Trp | Thr | Lys | Val | Gly | Asp | Val | Thr | Ala | Lys | Arg |
| | | 515 | | | | | 520 | | | | | 525 | | | |
| Met | Ser | Cys | His | Ala | Val | Ala | Ser | Gly | Asn | Lys | Leu | Tyr | Val | Val | Gly |
| | 530 | | | | | 535 | | | | | 540 | | | | |
| Gly | Tyr | Phe | Gly | Ile | Gln | Arg | Cys | Lys | Thr | Leu | Asp | Cys | Tyr | Asp | Pro |
| 545 | | | | | 550 | | | | | 555 | | | | | 560 |
| Thr | Leu | Asp | Val | Trp | Asn | Ser | Ile | Thr | Thr | Val | Pro | Tyr | Ser | Leu | Ile |
| | | | | 565 | | | | | 570 | | | | | 575 | |

| | | | | | | | | | | | | | | | | |
|---|---|---|---|---|---|---|---|---|---|---|---|---|---|---|---|---|
| Pro | Thr | Ala | Phe | Val | Ser | Thr | Trp | Lys | His | Leu | Pro | Ser | | | | |
| | | | 580 | | | | | 585 | | | | | | | | |

(2) INFORMATION FOR SEQ ID NO:3:

(i) SEQUENCE CHARACTERISTICS:
        (A) LENGTH: 1770 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..1767

(xi) SEQUENCE DESCRIPTION: SEQ ID NO:3:

| | | | | | | | | | | | | | | | | |
|---|---|---|---|---|---|---|---|---|---|---|---|---|---|---|---|---|
| ATG | TCA | GTC | AGT | GTG | CAT | GAG | AAC | CGC | AAG | TCC | AGG | GCC | AGC | AGT | GGC | 48 |
| Met | Ser | Val | Ser | Val | His | Glu | Asn | Arg | Lys | Ser | Arg | Ala | Ser | Ser | Gly | |
| 1 | | | | 5 | | | | | 10 | | | | | | 15 | |
| TCC | ATC | AAC | ATC | TAC | CTG | TTT | CAT | AAG | TCC | TCC | TAC | GCG | GAC | AGC | GTT | 96 |
| Ser | Ile | Asn | Ile | Tyr | Leu | Phe | His | Lys | Ser | Ser | Tyr | Ala | Asp | Ser | Val | |
| | | | 20 | | | | | 25 | | | | | 30 | | | |
| CTC | ACT | CAC | CTG | AAC | CTT | CTG | CGT | CAG | CAG | CGG | CTC | TTC | ACA | GAT | GTC | 144 |
| Leu | Thr | His | Leu | Asn | Leu | Leu | Arg | Gln | Gln | Arg | Leu | Phe | Thr | Asp | Val | |
| | | 35 | | | | | 40 | | | | | 45 | | | | |
| CTT | CTC | CAT | GCG | GGA | AAC | AGG | ACC | TTC | CCT | TGC | CAC | CGG | GCA | GTG | CTG | 192 |
| Leu | Leu | His | Ala | Gly | Asn | Arg | Thr | Phe | Pro | Cys | His | Arg | Ala | Val | Leu | |
| | 50 | | | | | 55 | | | | | 60 | | | | | |
| GCT | GCG | TGC | AGC | CGC | TAC | TTC | GAA | GCC | ATG | TTC | AGT | GGT | GGC | CTG | AAA | 240 |
| Ala | Ala | Cys | Ser | Arg | Tyr | Phe | Glu | Ala | Met | Phe | Ser | Gly | Gly | Leu | Lys | |
| 65 | | | | | 70 | | | | | 75 | | | | | 80 | |
| GAG | AGC | CAG | GAC | AGT | GAG | GTG | AAC | TTC | GAC | AAT | TCC | ATC | CAC | CCA | GAA | 288 |
| Glu | Ser | Gln | Asp | Ser | Glu | Val | Asn | Phe | Asp | Asn | Ser | Ile | His | Pro | Glu | |
| | | | | 85 | | | | | 90 | | | | | 95 | | |
| GTC | TTA | GAG | CTG | CTT | CTA | GAC | TAC | GCA | TAC | TCC | TCC | CGG | GTC | ATT | ATC | 336 |
| Val | Leu | Glu | Leu | Leu | Leu | Asp | Tyr | Ala | Tyr | Ser | Ser | Arg | Val | Ile | Ile | |
| | | | 100 | | | | | 105 | | | | | 110 | | | |
| AAT | GAA | GAA | AAT | GCT | GAG | TCG | CTC | CTG | GAG | GCT | GGT | GAC | ATG | CTG | GAG | 384 |
| Asn | Glu | Glu | Asn | Ala | Glu | Ser | Leu | Leu | Glu | Ala | Gly | Asp | Met | Leu | Glu | |
| | | 115 | | | | | 120 | | | | | 125 | | | | |
| TTC | CAG | GAC | ATC | AGA | GAT | GCG | TGT | GCA | GAA | TTT | CTA | GAG | AAG | AAC | CTG | 432 |
| Phe | Gln | Asp | Ile | Arg | Asp | Ala | Cys | Ala | Glu | Phe | Leu | Glu | Lys | Asn | Leu | |
| | 130 | | | | | 135 | | | | | 140 | | | | | |
| CAT | CCC | ACC | AAC | TGC | CTG | GGT | ATG | CTG | CTG | TTG | TCT | GAT | GCC | CAC | CAG | 480 |
| His | Pro | Thr | Asn | Cys | Leu | Gly | Met | Leu | Leu | Leu | Ser | Asp | Ala | His | Gln | |
| 145 | | | | | 150 | | | | | 155 | | | | | 160 | |
| TGC | ACC | AAG | CTG | TAC | GAA | CTC | TCC | TGG | AGA | ATG | TGT | CTC | AGC | AAC | TTC | 528 |
| Cys | Thr | Lys | Leu | Tyr | Glu | Leu | Ser | Trp | Arg | Met | Cys | Leu | Ser | Asn | Phe | |
| | | | | 165 | | | | | 170 | | | | | 175 | | |
| CAA | ACC | ATT | CGG | AAG | AAC | GAA | GAT | TTC | CTC | CAG | TTG | CCC | CAG | GAC | ATG | 576 |
| Gln | Thr | Ile | Arg | Lys | Asn | Glu | Asp | Phe | Leu | Gln | Leu | Pro | Gln | Asp | Met | |
| | | | 180 | | | | | 185 | | | | | 190 | | | |
| GTT | GTG | CAG | CTG | CTG | TCC | AGT | GAA | GAA | CTG | GAG | ACG | GAA | GAC | GAA | AGG | 624 |
| Val | Val | Gln | Leu | Leu | Ser | Ser | Glu | Glu | Leu | Glu | Thr | Glu | Asp | Glu | Arg | |
| | | 195 | | | | | 200 | | | | | 205 | | | | |
| CTG | GTG | TAT | GAG | TCT | GCG | ATG | AAC | TGG | ATC | AGC | TAT | GAC | CTG | AAG | AAG | 672 |
| Leu | Val | Tyr | Glu | Ser | Ala | Met | Asn | Trp | Ile | Ser | Tyr | Asp | Leu | Lys | Lys | |
| | | | 210 | | | | | 215 | | | | | 220 | | | |

| | | | | | | | | | | | | | | | | |
|---|---|---|---|---|---|---|---|---|---|---|---|---|---|---|---|---|
| CGC | TAC | TGT | TAC | CTC | CCG | GAA | CTG | TTG | CAG | ACA | GTG | AGG | CTG | GCC | CTC | 720 |
| Arg | Tyr | Cys | Tyr | Leu | Pro | Glu | Leu | Leu | Gln | Thr | Val | Arg | Leu | Ala | Leu | |
| 225 | | | | | 230 | | | | | 235 | | | | | 240 | |
| CTT | CCT | GCC | ATC | TAT | CTC | ATG | GAG | AAC | GTG | GCG | ATG | GAA | GAA | CTC | ATC | 768 |
| Leu | Pro | Ala | Ile | Tyr | Leu | Met | Glu | Asn | Val | Ala | Met | Glu | Glu | Leu | Ile | |
| | | | | 245 | | | | | 250 | | | | | 255 | | |
| ACC | AAG | CAG | AGA | AAG | AGT | AAG | GAG | ATC | GTG | GAA | GAG | GCC | ATC | AGG | TGC | 816 |
| Thr | Lys | Gln | Arg | Lys | Ser | Lys | Glu | Ile | Val | Glu | Glu | Ala | Ile | Arg | Cys | |
| | | | 260 | | | | | 265 | | | | | 270 | | | |
| AAA | CTA | AAA | ATC | TTA | CAG | AAT | GAC | GGC | GTG | GTC | ACC | AGT | CTC | TGT | GCT | 864 |
| Lys | Leu | Lys | Ile | Leu | Gln | Asn | Asp | Gly | Val | Val | Thr | Ser | Leu | Cys | Ala | |
| | | 275 | | | | | 280 | | | | | 285 | | | | |
| CGT | CCT | CGG | AAA | ACT | GGC | CAT | GCC | CTG | TTC | CTC | CTG | GGA | GGG | CAG | ACT | 912 |
| Arg | Pro | Arg | Lys | Thr | Gly | His | Ala | Leu | Phe | Leu | Leu | Gly | Gly | Gln | Thr | |
| 290 | | | | | 295 | | | | | 300 | | | | | | |
| TTC | ATG | TGT | GAC | AAA | CTG | TAC | TTG | GTA | GAC | CAG | AAG | GCT | AAA | GAA | ATC | 960 |
| Phe | Met | Cys | Asp | Lys | Leu | Tyr | Leu | Val | Asp | Gln | Lys | Ala | Lys | Glu | Ile | |
| 305 | | | | | 310 | | | | | 315 | | | | | 320 | |
| ATT | CCC | AAG | GCT | GAC | ATT | CCC | AGC | CCG | AGG | AAA | GAG | TTC | AGC | GCA | TGT | 1008 |
| Ile | Pro | Lys | Ala | Asp | Ile | Pro | Ser | Pro | Arg | Lys | Glu | Phe | Ser | Ala | Cys | |
| | | | | 325 | | | | | 330 | | | | | 335 | | |
| GCA | ATT | GGC | TGC | AAA | GTA | TAT | ATT | ACT | GGG | GGG | CGG | GGA | TCA | GAG | AAC | 1056 |
| Ala | Ile | Gly | Cys | Lys | Val | Tyr | Ile | Thr | Gly | Gly | Arg | Gly | Ser | Glu | Asn | |
| | | | 340 | | | | | 345 | | | | | 350 | | | |
| GGA | GTC | TCA | AAA | GAT | GTC | TGG | GTT | TAC | GAT | ACC | CTG | CAT | GAG | GAG | TGG | 1104 |
| Gly | Val | Ser | Lys | Asp | Val | Trp | Val | Tyr | Asp | Thr | Leu | His | Glu | Glu | Trp | |
| | | 355 | | | | | 360 | | | | | 365 | | | | |
| TCC | AAG | GCT | GCC | CCC | ATG | CTG | GTG | GCC | AGG | TTT | GGC | CAT | GGA | TCT | GCT | 1152 |
| Ser | Lys | Ala | Ala | Pro | Met | Leu | Val | Ala | Arg | Phe | Gly | His | Gly | Ser | Ala | |
| 370 | | | | | 375 | | | | | 380 | | | | | | |
| GAA | CTG | AAG | CAC | TGC | CTC | TAT | GTA | GTC | GGT | GGG | CAC | ACA | GCT | GCA | ACT | 1200 |
| Glu | Leu | Lys | His | Cys | Leu | Tyr | Val | Val | Gly | Gly | His | Thr | Ala | Ala | Thr | |
| 385 | | | | | 390 | | | | | 395 | | | | | 400 | |
| GGC | TGC | CTC | CCA | GCC | TCC | CCC | TCG | GTC | TCC | CTA | AAG | CAA | GTA | GAA | CAG | 1248 |
| Gly | Cys | Leu | Pro | Ala | Ser | Pro | Ser | Val | Ser | Leu | Lys | Gln | Val | Glu | Gln | |
| | | | | 405 | | | | | 410 | | | | | 415 | | |
| TAT | GAC | CCC | ACA | ACC | AAC | AAA | TGG | ACC | ATG | GTA | GCC | CCA | CTC | CGC | GAA | 1296 |
| Tyr | Asp | Pro | Thr | Thr | Asn | Lys | Trp | Thr | Met | Val | Ala | Pro | Leu | Arg | Glu | |
| | | | 420 | | | | | 425 | | | | | 430 | | | |
| GGT | GTC | AGC | AAT | GCT | GCT | GTA | GTG | AGT | GCC | AAA | CTT | AAG | CTG | TTT | GCT | 1344 |
| Gly | Val | Ser | Asn | Ala | Ala | Val | Val | Ser | Ala | Lys | Leu | Lys | Leu | Phe | Ala | |
| | | 435 | | | | | 440 | | | | | 445 | | | | |
| TTC | GGG | GGT | ACC | AGT | GTG | AGC | CAC | GAC | AAG | CTG | CCC | AAG | GTT | CAG | TGT | 1392 |
| Phe | Gly | Gly | Thr | Ser | Val | Ser | His | Asp | Lys | Leu | Pro | Lys | Val | Gln | Cys | |
| 450 | | | | | 455 | | | | | 460 | | | | | | |
| TAC | GAT | CAA | TGC | GAG | AAC | AGA | TGG | TCA | GTG | CCG | GCC | ACC | TGT | CCC | CAG | 1440 |
| Tyr | Asp | Gln | Cys | Glu | Asn | Arg | Trp | Ser | Val | Pro | Ala | Thr | Cys | Pro | Gln | |
| 465 | | | | | 470 | | | | | 475 | | | | | 480 | |
| CCC | TGG | CGT | TAC | ACA | GCC | GCA | GCT | GTG | CTG | GGA | AAC | CAG | ATT | TTT | ATC | 1488 |
| Pro | Trp | Arg | Tyr | Thr | Ala | Ala | Ala | Val | Leu | Gly | Asn | Gln | Ile | Phe | Ile | |
| | | | | 485 | | | | | 490 | | | | | 495 | | |
| ATG | GGT | GGA | GAT | ACA | GAG | TTC | TCT | GCC | TGC | TCC | GCT | TAC | AAA | TTC | AAT | 1536 |
| Met | Gly | Gly | Asp | Thr | Glu | Phe | Ser | Ala | Cys | Ser | Ala | Tyr | Lys | Phe | Asn | |
| | | | 500 | | | | | 505 | | | | | 510 | | | |
| AGT | GAG | ACT | TAC | CAG | TGG | ACC | AAG | GTG | GGA | GAT | GTG | ACA | GCC | AAG | CGC | 1584 |
| Ser | Glu | Thr | Tyr | Gln | Trp | Thr | Lys | Val | Gly | Asp | Val | Thr | Ala | Lys | Arg | |
| | | 515 | | | | | 520 | | | | | 525 | | | | |
| ATG | AGC | TGC | CAC | GCC | GTG | GCG | TCC | GGG | AAC | AAG | CTT | TAC | GTA | GTT | GGA | 1632 |
| Met | Ser | Cys | His | Ala | Val | Ala | Ser | Gly | Asn | Lys | Leu | Tyr | Val | Val | Gly | |
| 530 | | | | | 535 | | | | | 540 | | | | | | |

| | | | | | | | | | | | | | | | |
|---|---|---|---|---|---|---|---|---|---|---|---|---|---|---|---|
|GGG|TAC|TTC|GGC|ATT|CAG|CGC|TGC|AAG|ACT|TTG|GAC|TGT|TAC|GAC|CCA|
|Gly|Tyr|Phe|Gly|Ile|Gln|Arg|Cys|Lys|Thr|Leu|Asp|Cys|Tyr|Asp|Pro|
|545| | | |550| | | |555| | | |  | |560| |

1680

|ACT|TTA|GAT|GTG|TGG|AAC|AGC|ATA|ACC|ACT|GTT|CCC|TAC|TCT|CTG|ATC|
|---|---|---|---|---|---|---|---|---|---|---|---|---|---|---|---|
|Thr|Leu|Asp|Val|Trp|Asn|Ser|Ile|Thr|Thr|Val|Pro|Tyr|Ser|Leu|Ile|
| | | | |565| | | | |570| | | |575| | |

1728

|CCT|ACT|GCA|TTC|GTC|AGC|ACC|TGG|AAA|CAC|CTG|CCT|TCC|TAA|
|---|---|---|---|---|---|---|---|---|---|---|---|---|---|
|Pro|Thr|Ala|Phe|Val|Ser|Thr|Trp|Lys|His|Leu|Pro|Ser| |
| | | |580| | | | |585| | | | | |

1770

( 2 ) INFORMATION FOR SEQ ID NO:4:

( i ) SEQUENCE CHARACTERISTICS:
        ( A ) LENGTH: 589 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
|Met|Ser|Val|Ser|Val|His|Glu|Asn|Arg|Lys|Ser|Arg|Ala|Ser|Ser|Gly|
|1| | | |5| | | |10| | | | |15| |

| | | | | | | | | | | | | | | | |
|---|---|---|---|---|---|---|---|---|---|---|---|---|---|---|---|
|Ser|Ile|Asn|Ile|Tyr|Leu|Phe|His|Lys|Ser|Ser|Tyr|Ala|Asp|Ser|Val|
| | | |20| | | |25| | | |30| | | | |

|Leu|Thr|His|Leu|Asn|Leu|Leu|Arg|Gln|Gln|Arg|Leu|Phe|Thr|Asp|Val|
|---|---|---|---|---|---|---|---|---|---|---|---|---|---|---|---|
| | |35| | | | |40| | | | |45| | | |

|Leu|Leu|His|Ala|Gly|Asn|Arg|Thr|Phe|Pro|Cys|His|Arg|Ala|Val|Leu|
|---|---|---|---|---|---|---|---|---|---|---|---|---|---|---|---|
| |50| | | | |55| | | | |60| | | | |

|Ala|Ala|Cys|Ser|Arg|Tyr|Phe|Glu|Ala|Met|Phe|Ser|Gly|Gly|Leu|Lys|
|---|---|---|---|---|---|---|---|---|---|---|---|---|---|---|---|
|65| | | | |70| | | | |75| | | | |80|

|Glu|Ser|Gln|Asp|Ser|Glu|Val|Asn|Phe|Asp|Asn|Ser|Ile|His|Pro|Glu|
|---|---|---|---|---|---|---|---|---|---|---|---|---|---|---|---|
| | | | |85| | | | |90| | | | |95| |

|Val|Leu|Glu|Leu|Leu|Leu|Asp|Tyr|Ala|Tyr|Ser|Ser|Arg|Val|Ile|Ile|
|---|---|---|---|---|---|---|---|---|---|---|---|---|---|---|---|
| | | |100| | | | |105| | | |110| | | |

|Asn|Glu|Glu|Asn|Ala|Glu|Ser|Leu|Leu|Glu|Ala|Gly|Asp|Met|Leu|Glu|
|---|---|---|---|---|---|---|---|---|---|---|---|---|---|---|---|
| | |115| | | | |120| | | | |125| | | |

|Phe|Gln|Asp|Ile|Arg|Asp|Ala|Cys|Ala|Glu|Phe|Leu|Glu|Lys|Asn|Leu|
|---|---|---|---|---|---|---|---|---|---|---|---|---|---|---|---|
| |130| | | | |135| | | | |140| | | | |

|His|Pro|Thr|Asn|Cys|Leu|Gly|Met|Leu|Leu|Leu|Ser|Asp|Ala|His|Gln|
|---|---|---|---|---|---|---|---|---|---|---|---|---|---|---|---|
|145| | | | |150| | | | |155| | | | |160|

|Cys|Thr|Lys|Leu|Tyr|Glu|Leu|Ser|Trp|Arg|Met|Cys|Leu|Ser|Asn|Phe|
|---|---|---|---|---|---|---|---|---|---|---|---|---|---|---|---|
| | | | |165| | | | |170| | | | |175| |

|Gln|Thr|Ile|Arg|Lys|Asn|Glu|Asp|Phe|Leu|Gln|Leu|Pro|Gln|Asp|Met|
|---|---|---|---|---|---|---|---|---|---|---|---|---|---|---|---|
| | | |180| | | | |185| | | | |190| | |

|Val|Val|Gln|Leu|Leu|Ser|Ser|Glu|Glu|Leu|Glu|Thr|Glu|Asp|Glu|Arg|
|---|---|---|---|---|---|---|---|---|---|---|---|---|---|---|---|
| | |195| | | | |200| | | | |205| | | |

|Leu|Val|Tyr|Glu|Ser|Ala|Met|Asn|Trp|Ile|Ser|Tyr|Asp|Leu|Lys|Lys|
|---|---|---|---|---|---|---|---|---|---|---|---|---|---|---|---|
| |210| | | | |215| | | | |220| | | | |

|Arg|Tyr|Cys|Tyr|Leu|Pro|Glu|Leu|Leu|Gln|Thr|Val|Arg|Leu|Ala|Leu|
|---|---|---|---|---|---|---|---|---|---|---|---|---|---|---|---|
|225| | | | |230| | | | |235| | | | |240|

|Leu|Pro|Ala|Ile|Tyr|Leu|Met|Glu|Asn|Val|Ala|Met|Glu|Glu|Leu|Ile|
|---|---|---|---|---|---|---|---|---|---|---|---|---|---|---|---|
| | | | |245| | | | |250| | | | |255| |

|Thr|Lys|Gln|Arg|Lys|Ser|Lys|Glu|Ile|Val|Glu|Glu|Ala|Ile|Arg|Cys|
|---|---|---|---|---|---|---|---|---|---|---|---|---|---|---|---|
| | | |260| | | | |265| | | | |270| | |

|Lys|Leu|Lys|Ile|Leu|Gln|Asn|Asp|Gly|Val|Val|Thr|Ser|Leu|Cys|Ala|
|---|---|---|---|---|---|---|---|---|---|---|---|---|---|---|---|
| | |275| | | | |280| | | | |285| | | |

|Arg|Pro|Arg|Lys|Thr|Gly|His|Ala|Leu|Phe|Leu|Leu|Gly|Gly|Gln|Thr|
|---|---|---|---|---|---|---|---|---|---|---|---|---|---|---|---|

-continued

```
                    290                             295                             300
Phe   Met   Cys   Asp   Lys   Leu   Tyr   Leu   Val   Asp   Gln   Lys   Ala   Lys   Glu   Ile
305                           310                           315                           320
Ile   Pro   Lys   Ala   Asp   Ile   Pro   Ser   Pro   Arg   Lys   Glu   Phe   Ser   Ala   Cys
                        325                           330                           335
Ala   Ile   Gly   Cys   Lys   Val   Tyr   Ile   Thr   Gly   Gly   Arg   Gly   Ser   Glu   Asn
                  340                           345                           350
Gly   Val   Ser   Lys   Asp   Val   Trp   Val   Tyr   Asp   Thr   Leu   His   Glu   Glu   Trp
            355                           360                           365
Ser   Lys   Ala   Ala   Pro   Met   Leu   Val   Ala   Arg   Phe   Gly   His   Gly   Ser   Ala
      370                           375                           380
Glu   Leu   Lys   His   Cys   Leu   Tyr   Val   Val   Gly   Gly   His   Thr   Ala   Ala   Thr
385                           390                           395                           400
Gly   Cys   Leu   Pro   Ala   Ser   Pro   Ser   Val   Ser   Leu   Lys   Gln   Val   Glu   Gln
                        405                           410                           415
Tyr   Asp   Pro   Thr   Thr   Asn   Lys   Trp   Thr   Met   Val   Ala   Pro   Leu   Arg   Glu
                  420                           425                           430
Gly   Val   Ser   Asn   Ala   Ala   Val   Val   Ser   Ala   Lys   Leu   Lys   Leu   Phe   Ala
            435                           440                           445
Phe   Gly   Gly   Thr   Ser   Val   Ser   His   Asp   Lys   Leu   Pro   Lys   Val   Gln   Cys
      450                           455                           460
Tyr   Asp   Gln   Cys   Glu   Asn   Arg   Trp   Ser   Val   Pro   Ala   Thr   Cys   Pro   Gln
465                           470                           475                           480
Pro   Trp   Arg   Tyr   Thr   Ala   Ala   Ala   Val   Leu   Gly   Asn   Gln   Ile   Phe   Ile
                        485                           490                           495
Met   Gly   Gly   Asp   Thr   Glu   Phe   Ser   Ala   Cys   Ser   Ala   Tyr   Lys   Phe   Asn
                  500                           505                           510
Ser   Glu   Thr   Tyr   Gln   Trp   Thr   Lys   Val   Gly   Asp   Val   Thr   Ala   Lys   Arg
            515                           520                           525
Met   Ser   Cys   His   Ala   Val   Ala   Ser   Gly   Asn   Lys   Leu   Tyr   Val   Val   Gly
      530                           535                           540
Gly   Tyr   Phe   Gly   Ile   Gln   Arg   Cys   Lys   Thr   Leu   Asp   Cys   Tyr   Asp   Pro
545                           550                           555                           560
Thr   Leu   Asp   Val   Trp   Asn   Ser   Ile   Thr   Thr   Val   Pro   Tyr   Ser   Leu   Ile
                        565                           570                           575
Pro   Thr   Ala   Phe   Val   Ser   Thr   Trp   Lys   His   Leu   Pro   Ser
                  580                           585
```